United States Patent
Pang et al.

(10) Patent No.: US 11,672,827 B2
(45) Date of Patent: Jun. 13, 2023

(54) PHARMACEUTICAL CHIMERIC RECEPTOR COMPOSITION AND METHOD THEREOF

(71) Applicant: UWELL BIOPHARMA INC., New Taipei (TW)

(72) Inventors: Te-Ling Pang, Taipei (TW); Ming Chin Ko, Taitung (TW); Yi Han Dai, Tainan (TW); Yi-Ting Lai, Taichung (TW)

(*) Notice: Subject to any disclaimer, the term of this patent is extended or adjusted under 35 U.S.C. 154(b) by 197 days.

(21) Appl. No.: 16/955,766

(22) PCT Filed: Aug. 9, 2018

(86) PCT No.: PCT/CN2018/099502
§ 371 (c)(1),
(2) Date: Jun. 18, 2020

(87) PCT Pub. No.: WO2019/119822
PCT Pub. Date: Jun. 27, 2019

(65) Prior Publication Data
US 2021/0069244 A1   Mar. 11, 2021

Related U.S. Application Data

(60) Provisional application No. 62/610,156, filed on Dec. 23, 2017.

(51) Int. Cl.
| | | |
|---|---|---|
| *A61K 35/17* | (2015.01) | |
| *C07K 14/725* | (2006.01) | |
| *C07K 14/705* | (2006.01) | |
| *C07K 16/46* | (2006.01) | |
| *C12N 5/10* | (2006.01) | |
| *C12N 15/85* | (2006.01) | |

(52) U.S. Cl.
CPC .......... *A61K 35/17* (2013.01); *C07K 14/7051* (2013.01); *C07K 14/70517* (2013.01); *C07K 14/70525* (2013.01); *C07K 14/70578* (2013.01); *C07K 16/46* (2013.01); *C12N 5/10* (2013.01); *C12N 15/85* (2013.01)

(58) Field of Classification Search
CPC ................ A61K 35/17; C07K 14/7051; C07K 14/70517; C07K 14/70525; C07K 14/70578; C07K 16/46; C12N 5/10; C12N 15/85
See application file for complete search history.

(56) References Cited

U.S. PATENT DOCUMENTS

2019/0112380 A1*   4/2019   Chaudhary ............ A61K 35/17

FOREIGN PATENT DOCUMENTS

| CN | 105829536 A | 8/2016 |
|---|---|---|
| CN | 106279438 A | 1/2017 |
| CN | 106459924 A | 2/2017 |
| WO | WO2011028832 A2 | 3/2011 |
| WO | WO2012054748 A2 | 4/2012 |
| WO | WO2015157286 A1 | 10/2015 |
| WO | WO2015157297 A1 | 10/2015 |
| WO | WO2016130902 A1 | 8/2016 |

OTHER PUBLICATIONS

Yunlong Xing, International search report and written opinion by CNIPA as the International search authority, dated Nov. 13, 2018.
Office action and search report by TIPO, dated Feb. 5, 2020.
Office action by TIPO, dated Apr. 30, 2020.

* cited by examiner

*Primary Examiner* — Amy E Juedes
*Assistant Examiner* — Peter Johansen
(74) *Attorney, Agent, or Firm* — OPES IP Consulting Co. Ltd

(57) ABSTRACT

Disclosed herein are a pharmaceutical composition and a disease therapy method. The pharmaceutical composition relates to an artificial chimeric antigen receptor (CAR). Specifically, the pharmaceutical composition includes a CAR protein that is highly specific to CD19 antigen, a vector that is capable of inducing a cell to generate the certain CAR 19 protein and a population of a modified mammal cell including the CAR19 protein, the vector or combination thereof. Furthermore, the artificial CAR19 includes a CD19 antigen-binding fragment, a transmembrane domain, and a signaling domain. The CD19 antigen-binding fragment is a single-chain variable fragment (scFv) having specific amino acid sequences. Additionally, the method relates to a cancer therapy by using said modified mammal cells. Furthermore, the method includes the steps of purifying a population of autologous cells, modifying the population of autologous cells with an artificial CAR, and administrating the modified autologous cells.

10 Claims, 5 Drawing Sheets
Specification includes a Sequence Listing.

A

B

PHARMACEUTICAL CHIMERIC RECEPTOR COMPOSITION AND METHOD THEREOF

CROSS REFERENCE TO RELATED APPLICATIONS

The present application claims priority to PCT Application PCT/CN2018/099502 filed on Aug. 9, 2018, which claims priority to U.S. Provisional Application Ser. No. 62/610,156 filed on, Dec. 23, 2017, and the entire content of which is incorporated by reference to this application.

FIELD

The present disclosure relates to pharmaceutical chimeric receptor compositions. More particularly, it relates to pharmaceutical chimeric antigen receptor 19 compositions and therapy methods using such composition.

BACKGROUND

Cancer is a group of diseases characterized by the uncontrolled growth and spread of abnormal cells. If the growth and spread of cancer cells cannot be controlled, the host will die. Research shows that cancer is predominately caused by external factors such as tobacco, infectious organisms, and an unhealthy diet; and internal factors such as inherited genetic mutations, hormones, and immune conditions. These factors may act together or in sequence to cause cancer. Years may pass between the exposure to cancer causing factors and cancer detection. Cancer therapies may include surgery, radiation, chemotherapy, hormone therapy, immune therapy, and targeted therapy (drugs that interfere specifically with cancer cell growth).

Leukemia can be classified into four types: Acute Myeloblastic Leukemia (AML), Chronic Myeloblastic Leukemia (CIVIL), Acute Lymphoblastic Leukemia (ALL) and Chronic Lymphoblastic Leukemia (CLL). The major differences between the four types of leukemia are their progression rate and the location in which the cancer develops. According to the report from the Childhood Cancer Foundation, leukemia affects about 31% of the children with cancer, which is the highest of all cancer. Moreover, 95% of leukemia detected is acute leukemia.

Treatment strategies are different depending on the types leukemia (e.g., AML, CIVIL, ALL and CLL). Treatments may include chemotherapy, target therapy, radiation therapy, hematopoietic stem cell transplantation and/or supportive treatment. Because it is difficult to determine whether all leukemia cells in the host have been killed, recurrence of leukemain happens often. Also cancer cells may develop tolerance to regular chemotherapy.

The strategies for treating leukemia include chemotherapy, targeted therapy, radiotherapy, stem cells transplantation, support therapy, etc. Due to cancer recurrence and cells developing tolerance, immunoetherapy has recently become a popular alternative to conventional chemotherapy. One form of immunotherapy is to genetically modify T cells to target antigens expressed on tumor cells through the expression of chimeric antigen receptors (CARs). CARs are artificial designed antigen receptors that expressed on a human leucocyte through a genetic engineering to recognize tumor cell surface antigens. In 2011, Dr. Carl June successfully used modified T cells carrying CARs on the cell surface to treat leukemia patients. Porter et al., N Engl J Med, 2011; 365:725-733.

According to recent studies, tumor-specific antigens are not yet well defined in most tumors. However, it is well known that CD19 is an effective tumor target in B cell malignancies. Expression of CD19 is restricted to normal and malignant B cells (Uckun, et al. Blood, 1988, 71:13-29). Also, some studies demonstrated that it is effective to eliminate B lymphoma through targeting CD19. See for example, Salem et al., Indian J Hematol Blood Transfus, 2012, 28(2):89-96; Schewe et al., Blood, 2017-01-764316; and Seidel et al., Mol Ther., 2016, 24(9):1634-43.

Therefore, there is a need to develop a pharmaceutical CAR composition containing small protein with highly specific recognition to CD19, and an effective method to treat patient with abundant CD19 expression by using such pharmaceutical CAR composition.

SUMMARY

The present disclosure provides an artificial CAR protein including a CD19 antigen-binding fragment, a transmembrane domain, and a signaling domain. Further, the CD19 antigen-binding fragment is a single-chain variable fragment (scFv) including a heavy chain variable domain, a light chain variable domain and at least one linker between the heavy and the light chain variable domains. The heavy chain variable domain includes a first amino acid sequence selected from SEQ ID NO: 8, SEQ ID NO: 10, SEQ ID NO: 12 or any combination thereof, and the light chain variable domain includes a second amino acid sequence selected from SEQ ID NO: 7, SEQ ID NO: 9, SEQ ID NO: 11 or any combination thereof. The transmembrane domain includes a transmembrane domain of CD28, IgG1, CD4, CD8α or any combination thereof. The signaling domain includes at least one immunoreceptor tyrosine-based activation motif (ITAM), at least one co-stimulatory molecule (CM) or the combination thereof.

In some embodiments of the present disclosure, the transmembrane domain of the artificial CAR protein is the transmembrane domain of CD8a.

In some embodiments of the present disclosure, the artificial CAR protein includes at least two CMs.

In some embodiments of the present disclosure, the at least one ITAM of the artificial CAR protein includes the CD3 zeta.

In some embodiments of the present disclosure, the at least one CM of the artificial CAR protein includes a CM of CD27, CD28, 4-1BB/CD137, OX40 herpesvirus entry mediator (HVEM) or any combination thereof.

In some embodiments of the present disclosure, the at least one CM of the artificial CAR protein includes the CM of 4-1BB/CD137.

The present disclosure also provides an expression vector of artificial CAR having a CD19 antigen-binding fragment sequence, a transmembrane domain sequence and a signaling domain sequence. Further, the CD19 antigen-binding fragment sequence includes a heavy chain variable domain nucleic acid sequence, a light chain variable domain nucleic acid sequence and at least one linker between the heavy and the light chain variable domain nucleic acid sequences. The nucleic acid sequence of the heavy chain variable domain includes SEQ ID NO: 2, SEQ ID NO: 4, SEQ ID NO: 6 or any combination thereof, and the nucleic acid sequence of the light chain variable domain includes SEQ ID NO: 1, SEQ ID NO: 3, SEQ ID NO: 5 or any combination thereof. The transmembrane domain sequence includes a transmembrane sequence of CD28, IgG1, CD4, CD8α or any combination thereof. The signaling domain sequence includes at least one ITAM sequence, at least one CM sequence or the combination thereof.

The present disclosure further provides a pharmaceutical composition having a population of a modified cell. Specifically, the modified cell includes at least one artificial CAR protein, at least one artificial CAR expression vector or the combination thereof, both of which having the specific property as the previous description respectively.

In some embodiments of the present disclosure, the modified cell of the pharmaceutical composition is a mammalian cell.

In some embodiments of the present disclosure, the modified cell of the pharmaceutical composition is a lymphocyte.

In some embodiments of the present disclosure, the modified cell of the pharmaceutical composition is a T cell or a NK cell.

The present disclosure furthermore provides a method for treating a mammal having a disease, disorder or a condition associated with an elevated expression of a CD19 antigen. Specifically, the method includes the following steps: step (a) isolating peripheral blood from at least one mammal; step (b) purifying a plurality of lymphocytes from the peripheral blood; step (c) generating a pharmaceutical composition having at least one artificial CAR protein, at least one artificial CAR expression vector or the combination thereof using the lymphocyte; step (d) treating the mammalian recipient with at least one of chemotherapeutic agent; and step (e) administrating the pharmaceutical composition to the mammalian recipient.

In some embodiments of the present disclosure, the step (c) further includes a step of amplifying the pharmaceutical composition.

In some embodiments of the present disclosure, the pharmaceutical composition is autologous to at least one of the mammalian donor and at least one of the mammalian recipient.

In some embodiments of the present disclosure, the pharmaceutical composition is allogenic to at least one of the mammalian donor and at least one of the mammalian recipient.

In some embodiments of the present disclosure, the lymphocyte isolated from the peripheral blood is a T cell or a NK cell.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

FIG. 1A illustrates the lentiviral vectors and transgene that show the major functional elements. A lentiviral vector (pLAS5w.PeGFP-I2-Puro) directing expression of anti-CD19 seFv derived from murine or human monoclonal antibody, human CD8α hinge and transmembrane domain, as well as human 4-1BB/CD137 and CD3zeta signaling domains, were produced. Constitutive expression of the transgene was directed by the inclusion of an EF-1α (elongation factor-1a promoter); LTR, long terminal repeat; RRE, rev response element; IRES, internal ribosome entry site; eGFP, enhanced green fluorescence protein; and WPRE, woodchunk hepatitis virus post transcriptional regulatory element. FIG. 1B illustrates CD3 and CD56 expression of purified PBMCs and lymphocytes by surface staining. Further, the upward shift (on Y-axis) in the FACS staining pattern is due to the CD3 expression on the purified cells, and the right shift (on X-axis) in the FACS staining pattern is due to the CD56 expression on cells.

FIGS. 2A and 2B depict Fab and GFP expression on the modified $CD3^+$ lymphocytes after the construction by surface staining. Furthermore, as FIG. 2A shows, the upward shift in the FACS staining pattern is due to the Fab expression on the purified cells, and the right shift in the FACS pattern is due to lentivirial vector incorporation of the modified $CD3^+$ lymphocytes. FIG. 2B depicts statistic data of the expression of Fab or GFP on the modified $CD3^+$ lymphocytes after construction. Each data bar represents the average of triplicate measurement of the Fab expression or the GFP expression on each modified lymphocytes. FIG. 2C depicts the statistic data of the cell number fold of various modified $CD3^+$ lymphocytes in different time points after construction. Each data point represents the average of triplicate measurement of the modified lymphocytes.

FIGS. 3A and 3B depict the remaining quantity of RS4;11 or Raji cells after co-culturing with the different modified $CD3^+$ lymphocytes for 24 hours by surface staining. Furthermore, as FIGS. 3A and 3B show, the right shift of gating area in the FACS staining pattern is due to the CD19 positive expression on RS4;11 or Raji cells. FIGS. 3C and 3D depict statistic data of the remaining quantity of RS4;11 or Raji cells after co-culturing with the different modified $CD3^+$ lymphocytes. Each bar represents the average of triplicate measurement of the $CD19^+$ cells. FIGS. 3E and 3F depict interferon-γ (INF-γ) secretion ability of the different modified $CD3^+$ lymphocytes to RS4;11 or Raji cells after co-culture for 24 hours by enzyme-linked immunosorbent assay. Each bar represents the average of triplicate measurement of the quantity of INF-γ.

FIG. 4A depicts the cytotoxic quantity of the different modified $CD3^+$ lymphocytes in response to a different ratio (E:T, CAR19 T cells versus target tumor cells) of allogeneic lymphoma cells ($CD19^+$ cells: RS4;11 and Raji; and $CD19^-$ cells K562) after 4 hours co-culture. Each data point represents the average of triplicate measurement of the modified lymphocytes. FIG. 4B shows that the UW022 transfected CD3+ lymphocytes release the most interferon-γ (INF-γ) after co-culturing with the RS4;11 or Raji cells for 4 hours.

FIG. 5A depicts the in vivo experiment design. NOD/SCID mice were given Raji/$Luc^+$ cells at Day 0 and different modified $CD3^+$ lymphocytes at Day 7. After, the NOD/SCID mice are imaged by the IVIS system every seven days. FIG. 5B depicts the tumor (Raji/$Luc^+$ cells) growth at the respective time point by an in vivo imaging system. FIG. 5C depicts statistic data of the bioluminescence intensity (BLI) of the tumor size monitored by the in vivo imaging system. Each data bar represents the average of five repeated measurement of the BLI value.

Figure 1:
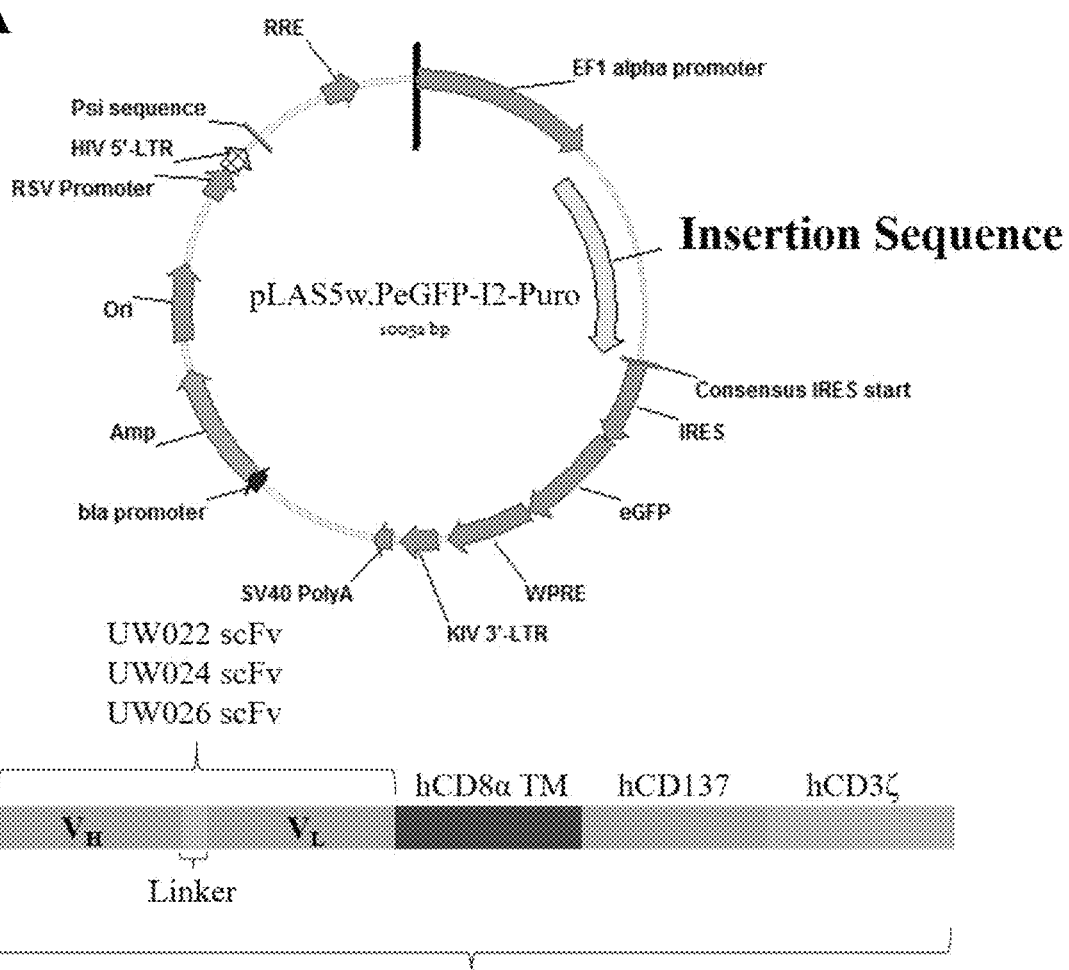
FIGS. 1A-1B are images of the schematic representations of the gene-transfer vector and transgene and the purity of PBMCs and lymphocytes purification.
Figure 1:
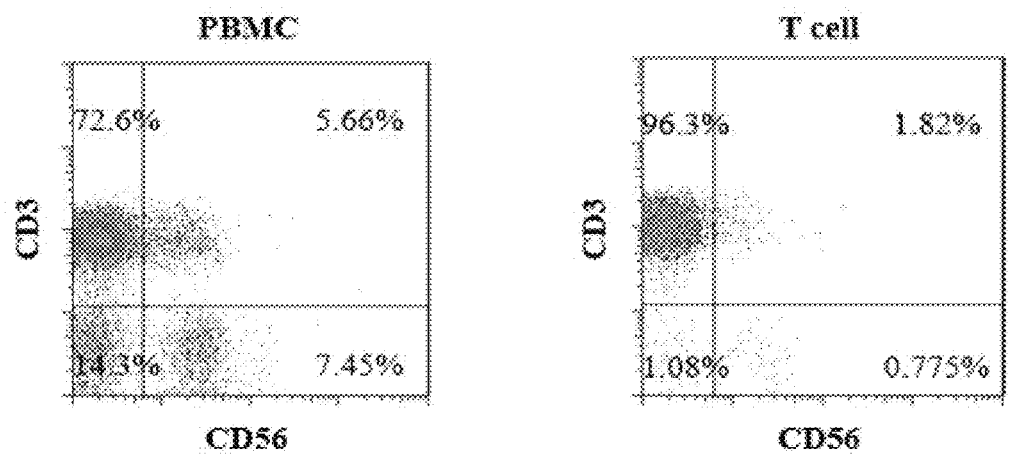

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention. Any reference signs in the claims shall not be construed as limiting the scope. Like reference symbols in the various drawings indicate like elements.

DETAILED DESCRIPTION OF THE DISCLOSURE

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

The present disclosure relates to compositions and a method for treating disorders or diseases, such as cancer including but not limited to hematologic malignancies and solid tumors. The present disclosure relates to a strategy of constructing an artificial CAR protein, an expression vector of the artificial CAR and a pharmaceutical composition that may include molecules thereof that combine antibody-based specificity for a desired antigen (e.g., tumor antigen) with a T cell receptor-activating intracellular domain to generate a chimeric protein that exhibits a specific anti-tumor cellular immune activity.

The present disclosure generally relates to a protein construction of genetically modified CAR. Moreover, the artificial CAR of the present disclosure is highly specific to the CD19 antigen. Therefore, the artificial CAR is referred to herein as CAR19 or anti-CD19 CAR.

The artificial CAR19 protein of the present composition generally includes three major domains located in an extracellular area, a cell membrane area and an intracellular area respectively. The three major domains include a CD19 antigen-binding fragment, a transmembrane domain and a signaling domain. Further, the CD19 antigen-binding fragment is a scFv having a heavy chain variable domain and a light chain variable domain as well as a linker to connect the variable domain of heavy chain and light chain. Additionally, the heavy chain variable domain includes a first amino acid sequence, which is selected from SEQ ID NO: 8, SEQ ID NO: 10, SEQ ID NO: 12 or any combination thereof. The light chain variable domain may include a second amino acid sequence, which is selected from SEQ ID NO: 7, SEQ ID NO: 9, SEQ ID NO: 11 or any combination thereof. In another aspect, the transmembrane domain includes a transmembrane domain of CD28, IgG1, CD4, CD8α or any combination thereof. In the other aspect, the signaling domain includes at least one ITAM, at least one CM or the combination thereof.

In some embodiments, the artificial CAR19 protein of the present composition consists of the CD19 antigen-binding fragment, the transmembrane domain and the signaling domain. That is, the CAR19 protein only includes these three domains without any other domain. Moreover, the scFv also only includes one heavy chain variable domain, one light chain variable domain and one linker therebetween. Similarly, the first amino acid sequence of the heavy chain variable domain is selected from SEQ ID NO: 8, SEQ ID NO: 10 or SEQ ID NO: 12. The second amino acid sequence of the light chain variable domain is selected from SEQ ID NO: 7, SEQ ID NO: 9 or SEQ ID NO: 11. In another aspect, the transmembrane domain only includes a transmembrane domain of the CD28, IgG1, CD4 or CD8a. In the other aspect, the signaling domain only includes an ITAM or a CM.

In some embodiments, the scFv of the CD19 antigen-binding fragment further includes a linker sequence selected from SEQ ID NO: 13, SEQ ID NO: 14, SEQ ID NO: 15 or SEQ ID NO: 16. An another embodiments, the artificial CAR19 protein further includes at least one linker between two protein domains others than the CD19 antigen-binding fragment, and the linker includes a sequence selected from SEQ ID NO: 13, SEQ ID NO: 14, SEQ ID NO: 15 or SEQ ID NO: 16.

In some embodiments, the artificial CAR19 protein includes at least two CD19 antigen-binding fragments. That is, there are more than one scFv molecule. The first amino acid sequence of the heavy chain variable domain may be a repeated sequence or any combination sequence selected form SEQ ID NO: 7, SEQ ID NO: 9 or SEQ ID NO: 11. Also, the second amino acid sequence of the light chain variable domain may be a repeated sequence of or any combination sequence of SEQ ID NO: 7, SEQ ID NO: 9 or SEQ ID NO: 11.

In some embodiments, the scFv of the artificial CAR19 protein composition includes a specific combination of the first amino acid sequence and the second amino acid sequence, which is the SEQ ID NO: 8 with SEQ ID NO: 7, the SEQ ID NO: 10 with SEQ ID NO: 9, or the SEQ ID NO: 12 with SEQ ID NO: 11.

In some preferable embodiments, the artificial CAR19 protein includes the first amino acid sequence of the heavy chain variable domain that is the SEQ ID NO: 8, and the second amino acid sequence of the light chain variable domain that is the SEQ ID NO: 7.

In some preferable embodiments, the transmembrane domain of the artificial CAR19 protein is the transmembrane domain of CD8a.

In some embodiments, the signaling domain of the artificial CAR19 protein includes both the ITAM and the CM. In another embodiment, the combination of the signaling domain of the artificial CAR19 protein includes at least one ITAM and at least two CM.

In some embodiments, the at least one ITAM of the signaling domain in the artificial CAR19 protein is a CD3 zeta chain.

In some embodiments, the CM of the signaling domain in the artificial CAR19 protein includes a CM region of CD27, CD28, CD30, 4-1BB/CD137, OX40 or HVEM. In another embodiment, the number of the CM of the signaling domain is at least two, therefore, the CMs include any combination of the CM regions of CD27, CD28, CD30, 4-1BB/CD137, OX40 or HVEM. In one preferable embodiment, the artificial CAR19 protein includes one CM in the signaling domain, and the CM is 4-1BB/CD137 or CD28.

The present disclosure also relates to an expression vector that may express a desired artificial CAR19 stably. A backbone of the artificial CAR19 expression vector generally is selected from the expression vector system used in the mammalian system. Preferably, the expression vector is a lentiviral vector. Further, the artificial CAR19 expression vector includes a CD19 antigen-binding fragment sequence, a transmembrane domain sequence and a signaling domain sequence. In one aspect, the CD19 antigen-binding fragment sequence includes a nucleic acid sequence of a heavy chain variable domain, a nucleic acid sequence of a light chain variable domain and a linker. The nucleic acid sequence of heavy chain variable domain includes SEQ ID NO: 2, SEQ ID NO: 4, SEQ ID NO: 6 or any combination thereof, and the nucleic acid sequence of light chain variable domain includes SEQ ID NO: 1, SEQ ID NO: 3, SEQ ID NO: 5 or any combination thereof. In another aspect, the transmembrane domain sequence includes a transmembrane sequence of CD28, IgG1, CD4, CD8α or any combination thereof. In the other aspect, the signaling domain sequence comprises an ITAM sequence, a CM sequence or the combination thereof.

In some embodiments, the artificial CAR19 expression vector consists a nucleic acid sequence of a vector backbone, a CD19 antigen-binding fragment, a transmembrane domain and a signaling domain. That is, the CAR19 expression vector only includes these four nucleic acid sequences without any other nucleic acid sequence. Further, the CD19 antigen-binding fragment sequence is consisted of three nucleic acid sequences. That is, the CD19 antigen-binding fragment sequence only includes the sequences of the heavy chain variable domain, the light chain variable domain and the linker. The transmembrane domain sequence only consists of one sequence, which is the transmembrane sequence of CD28, IgG1, CD4 or CD8a. The signaling domain sequence also only consists of a single sequence, which is the CM sequence or the ITAM sequence.

In some embodiments, the artificial CAR19 expression vector includes more than one (i.e., at least two) nucleic acid sequence of the heavy chain variable domain or the light chain variable domain. In another word, the nucleic acid sequence of the heavy chain variable domain may be a repeat of or any combination of SEQ ID NO: 2, SEQ ID NO: 4 or SEQ ID NO: 6, and the nucleic acid sequence of the light chain variable domain may be a repeat of or any combination of SEQ ID NO: 1, SEQ ID NO: 3 or SEQ ID NO: 5.

In some embodiments, the artificial CAR19 expression vector includes a specific nucleic acid sequence combination of the heavy chain variable domain and the light chain variable domain, and the combination is SEQ ID NO: 2 with SEQ ID NO: 1, SEQ ID NO: 4 with SEQ ID NO: 3, or SEQ ID NO: 6 with SEQ ID NO: 5.

In one preferable embodiment, a nucleic acid sequence of the heavy chain variable domain and the light chain variable domain of the artificial CAR19 expression vector are SEQ ID NO: 2 and SEQ ID NO: 1, respectively.

In some embodiments, a transmembrane domain sequence of the artificial CAR19 expression vector includes at least two transmembrane sequences. Therefore, the transmembrane domain sequence may be a repeated sequence of or any combination sequence of the transmembrane sequence of CD28, IgG1, CD4 or CD8a.

In some embodiments, the signaling domain sequence of the artificial CAR19 expression vector includes a repeated sequence of or any combination sequence of the ITAM sequence or the CM sequence. That is, the numbers of the ITAM sequence or the CM sequence is at least two.

In one preferable embodiment, the transmembrane domain sequence of the artificial CAR19 expression vector is the transmembrane sequence of CD8a.

In one preferable embodiment, the ITAM sequence of the signaling domain sequence of the artificial CAR19 expression vector is a CD3 zeta chain.

In some embodiments, the CM sequence of the artificial CAR19 expression vector includes a CM sequence of CD27, CD28, CD30, 4-1BB/CD137, OX40 or HVEM. In another embodiment, the number of the CM sequence of the signaling domain sequence is at least two, therefore the CM sequences include a repeated sequence of or any combination sequence of the CM sequences of CD27, CD28, CD30, 4-1BB/CD137, OX40 or HVEM. In one preferable embodiment, the artificial CAR19 expression vector includes one CM sequence, which is the CM sequence of 4-1BB/CD137 or CD28.

The present invention further relates to a pharmaceutical composition including a population of genetically modified cell stably expresses at least one artificial CAR19 protein or at least one expression vector of the artificial CAR19 with the specific properties as mentioned previously. In another embodiment, the genetically modified cell of the pharmaceutical composition not only stably express the at least one artificial CAR19 protein but also the at least one expression vector of the artificial CAR19.

In another embodiment, the pharmaceutical composition consists of the population of the genetically modified cell, the genetically modified cell stably expressed the at least one artificial CAR19 protein or included the at least one expression vector of the artificial CAR19. In other words, the pharmaceutical composition only has the modified cell in it and without any other pharmaceutical component (e.g., cancer drug). Furthermore, the modified cell may expresses the artificial CAR19 protein, the artificial CAR19 expression vector or both.

In some embodiments, the modified cell used in the pharmaceutical composition is a mammalian cell. In another embodiment, the modified cell used in the pharmaceutical composition is a lymphocyte. Furthermore, in one preferred embodiment, the modified cell used in the pharmaceutical composition is a CD3+ lymphocyte, for example, a T cell.

The present invention further relates to a therapeutic method of treating a mammal having a disease, disorder or a condition associated with an elevated expression of an antigen. In one aspect, the disease preferably is cancer, e.g. CLL. In another aspect, the elevated expression of the antigen preferably is a CD19 antigen. The therapeutic method generally includes the following steps. In step (a), peripheral blood is isolated from at least one mammalian donor, and lymphocytes is further purified from the peripheral blood in step (b). In step (c), the purified lymphocytes is further used to generate a pharmaceutical composition. Step (d) relates to treating at least one mammalian recipient with at least one chemotherapeutic agent. Then, administering the pharmaceutical composition to the at least one mammalian recipient. Specifically, the pharmaceutical composition in the therapeutic method is the population of the lymphocytes that may express at least one artificial CAR19 protein or carry at least one artificial CAR19 expression vector with the specific properties as previously described. In some embodiments, the lymphocytes not only express the at least one artificial CAR19 protein but also carries at least one artificial CAR19 expression vector.

In another embodiment, the therapeutic method only consists the step (a) to the step (e) as the previously described. That is, there are only five steps in the therapeutic method of treating a mammal having the disease (e.g., cancer).

In some embodiments, the step (c) of the therapeutic method further includes a step that amplifies the pharmaceutical composition.

In some embodiments, the pharmaceutical composition used in the therapeutic method is autologous to at least one mammalian donor and one mammalian recipient. In other words, the modified lymphocytes of the pharmaceutical composition is purified from a mammalian donor and then readministrated back to the mammalian donor after engineering. In another embodiment, the pharmaceutical composition used in the therapeutic method is allologous to at least one mammalian donor and one mammalian recipient. That is a mammalian donor is different from a mammalian recipient.

In one preferred embodiment, the lymphocyte of the pharmaceutical composition used in the therapeutic method is $CD3^+$ lymphocyte (i.e., T cells) or $CD56^+$ lymphocyte (i.e., NK cells).

DEFINITION

Throughout the various views and illustrative embodiments, like reference numerals are used to designate like elements. Reference will now be made in detail to exemplary embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, an apparatus by the present disclosure. It is to be understood that elements not specifically shown or described may take various forms. Reference throughout this specification to "one embodiment" or "an embodiment" means that a particular feature, structure, or characteristic described in connection with the embodiment is included in at least one embodiment. Thus, the appearances of the phrases "In some embodiments" or "in an embodiment" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are merely intended for illustration.

In the drawings, like reference numbers are used to designate like or similar elements throughout the various views, and illustrative embodiments of the present disclosure are shown and described. The figures are not necessarily drawn to scale, and in some instances the drawings have been exaggerated and/or simplified in places for illustrative purposes. One of ordinary skill in the art will appreciate the many possible applications and variations of the present disclosure based on the following illustrative embodiments of the present disclosure.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

The term "about," as used herein, when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds to an antigen. Antibodies can be intact immunoglobulins derived from natural sources or recombinant sources and can be immunoreactive portions of intact immunoglobulins. Antibodies are typically tetramers of immunoglobulin molecules. The antibodies of the present invention may exist in a variety of forms including, for example, polyclonal antibodies, monoclonal antibodies, Fv, Fab and F(ab)2, as well as single chain antibodies and humanized antibodies.

The term "antibody fragment" refers to a portion of an intact antibody and refers to the antigenic determining variable regions of an intact antibody. Examples of antibody fragments include, but are not limited to, Fab, F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" or "anti-tumor" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

As used herein, the term "allologous" is meant to refer to any material derived from the different individual to which it is later to be re-introduced into the individual.

The term "allogeneic" refers to a graft derived from a different animal of the same species.

The term "xenogeneic" refers to a graft derived from an animal of a different species.

The term "cancer" as used herein is defined as a disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., dendritic cells, B cells, and the like) that specifically binds a cognate co-stimulatory molecule on a T cell and provides a signal. The signal, in addition to the primary signal provided by binding of a TCR/CD3 complex with an MEW molecule loaded with peptide, mediates a T cell response. The cell response includes, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds to a co-stimulatory ligand, thereby mediating a co-stimulatory response by the T cell, such as, but not limited to, proliferation. Co-stimulatory molecules include, but are not limited to an MHC class 1 molecule, BTLA and a Toll ligand receptor.

A "co-stimulatory signal", as used herein, refers to a signal, which in combination with a primary signal, such as TCR/CD3 ligation, leads to T cell proliferation and/or up-regulation or down regulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or a mRNA, to serve as templates for synthesis of other polymers and macromolecules in biological processes. The templates have either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing the release of mediators from mast cells and basophils upon exposure to the allergen.

"Isolated" as used herein means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "hyperexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

The term "administration of" or "administering" an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types, "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein concerning an antibody, is meant an antibody which recognizes a specific antigen, but does not substantially recognize or bind other molecules in a sample. For example, an antibody that specifically binds to an antigen from one species may also bind to that antigen from one or more species. However, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "stimulation" or "amplification" is meant a primary response induced by binding of a stimulatory molecule (e.g., a TCR/CD3 complex) with its cognate ligand thereby mediating a signal transduction event, such as, but not limited to, signal transduction via the TCR/CD3 complex. Moreover, the term "stimulate" or "amplify" is used to describe the process that using the stimulatory ligand to trigger the primary response. Further, the terms "stimulate" and "amplify" are interchangeable. Stimulation can mediate altered expressions of certain molecules, such as down-regulation of TGF-β, and/or reorganization of cytoskeletal structures, and the like.

The term "generating" or "amplifying" a composition, means to increase the quantity of the composition, e.g. a cell number. Hence, the term "generating" and "amplifying" are interchangeable.

A "stimulatory molecule," as the term is used herein, means a molecule on a T cell that specifically binds to a cognate stimulatory ligand present on an antigen presenting cell.

A "stimulatory ligand," as used herein, means a ligand that when present on an antigen presenting cell (e.g., an APC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter cilia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to a cell that has been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. Therefore, as describing the transfer process, these three words are interchangeable. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate the transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Description

The present invention provides compositions and a method for treating a disease, disorder or a condition. More specifically, the disease includes cancer which may be a hematological malignancy, a solid tumor, a primary or a metastasis tumor. Preferably, the cancer is a hematological malignancy, and more preferably, the cancer is Chronic Lymphocytic Leukemia (CLL). Other diseases that may be treated with the administration of the compositions of the present invention include viral, bacterial, parasitic infections or autoimmune diseases.

Protein Composition

One of the compositions of the present invention is an artificial CAR protein that includes three portions, i.e. an extracellular domain, a transmembrane domain and an intracellular domain. The extracellular domain includes a target-specific binding element otherwise referred to as an antigen binding moiety. The transmembrane domain links the extracellular domain and the intracellular domain, while also supports the extracellular domain on the cell surface. The intracellular domain or otherwise the cytoplasmic domain includes a signaling domain. The signaling domain further includes at least one ITAM region, at least one CM, or any combination thereof. The CM is a cell molecule other than an antigen receptor that is required for an efficient response of lymphocytes to antigen.

Within the extracellular domain or the cytoplasmic domain of the CAR, between the extracellular domain and the transmembrane domain of the CAR, or between the cytoplasmic domain and the transmembrane domain of the CAR, at least one linker or spacer domain may be incorporated. As used herein, the term "linker" generally means any oligo- or polypeptide that functions to link protein domains in the polypeptide chain. A linker may include about 300 amino acids, preferably about 10 to 100 amino acids, preferably about 10 to 50 amino acids and most preferably about 25 to 50 amino acids.

Antigen Binding Moiety

In some embodiments, the CAR of the invention comprises a target-specific binding element otherwise referred to as an antigen binding moiety that can be recognized by a synthetic antibody. The choice of moiety depends upon the type and number of ligands that define the surface of a target cell. For example, the antigen binding domain may recognize a ligand that acts as a cell surface marker on target cells associated with a particular disease state. Examples of cell surface markers that may act as ligands for the antigen binding moiety in the CAR of the present invention include those associated with viral, bacterial and parasitic infections, autoimmune disease and cancer cells.

In some embodiments, the CAR of the present invention can be engineered to target a tumor antigen of interest by way of engineering a desired antigen binding moiety that specifically binds to an antigen on a tumor cell. In the context of the present invention, "tumor antigen" or "hyper-expression disorder antigen" or "antigen associated with a hyper-expression disorder," refers to antigens that are common to specific hyper-expression disorders such as cancer. The antigens discussed herein are merely included as examples. The list is not intended to be exclusive and other examples are readily apparent to those of skill in the art.

Tumor antigens are proteins that are produced by tumor cells that elicit an immune response, particularly T-cell mediated immune response. The selection of the antigen binding moiety of the present invention will depend on the particular type of cancer to be treated. In some embodiments, the tumor antigen comprises one or more antigenic cancer epitopes associated with a malignant tumor. Malignant tumors express numbers of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as oncogene HER-2/Neu/ErbB-2. Another group of target antigens is onco-fetal antigens such as carcinoembryonic antigen (CEA). In B-cell lymphoma, the tumor-specific idiotype immunoglobulin constitutes a truly tumor-specific immunoglobulin antigen that is unique to the individual tumor. B-cell differentiation antigens such as hemagglutinin protein of influenza virus, hen egg lysozyme, ovalbumin, CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the present invention may also be a tumor-specific antigen (TSA) or a tumor-associated antigen (TAA). A TSA is unique to tumor cells and does not express on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that present at extremely low levels in normal cells but which are expressed at much higher levels in tumor cells.

Depending on the desired antigen to be targeted, the CAR of the present invention can be engineered to include the appropriate antigen bind moiety that is specific to the desired antigen target. For example, if CD19 is the desired antigen, which is the target antigen, an antibody for CD19 can be used as the antigen bind moiety to be incorporated into the CAR of the present invention.

Transmembrane Domain

The CAR of the present invention can be designed to comprise a transmembrane domain that is fused to the extracellular domain (e.g., the antigen binding moiety) of the CAR. In some embodiments, the transmembrane domain that naturally associates with one of the domains in the CAR is used. For example, the transmembrane domain can be selected or modified by amino acid substitution to avoid binding of such domains to the transmembrane domains of the same or different surface membrane proteins to minimize interactions with other members of the receptor complex. In another embodiment, the transmembrane domain does not directly connect or link to any domain of the antigen bind moiety. Therefore, there is at least one short peptide (e.g., linker) between the transmembrane domain and the antigen bind moiety.

The transmembrane domain may be derived either from a natural or a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, IgG1, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In some embodiments, the transmembrane domain in the CAR of the present invention is CD28, IgG1, CD4, CD8α or any combination thereof. In a preferred embodiment, the transmembrane domain of the CAR is the transmembrane domain of CD8a.

Signaling Domain

The signaling domain or otherwise the cytoplasmic domain of the CAR of the present invention is responsible for activating at least one of the normal effector functions of the immune cell. The term "effector function" refers to a specialized immune function of an immune cell. Effector function of a lymphocyte cell, more specifically a CD3+ lymphocyte, may be a cytolytic activity or helper activity including the secretion of cytokines. The term "signaling domain" refers to the portion of a protein which transduces the effector function signal and directs the cell to perform a specialized function. While usually the entire intracellular signaling domain can be employed, in many cases it is not necessary to use the entire protein. To the area that is being used as a truncated portion of the signaling domain, such truncated portion may be used in place of the whole protein as long as it transduces the effector function signal. Therefore, the term signaling domain is meant to include any truncated portion of the signaling domain sufficient to transduce the effector function signal.

Preferred examples of signaling domains for use in the CAR of the present invention include the cytoplasmic sequences of the T cell receptor (TCR) and co-receptors. Both of these domain act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation is mediated by two distinct classes of signaling sequence: those that initiate antigen-dependent primary activation through the TCR (primary signaling sequences) and those that act in an antigen-independent manner to provide a secondary or co-stimulatory signal (secondary signaling sequences).

Primary signaling domains regulate primary activation of the TCR complex either in a stimulatory way, or in an inhibitory way. Primary signaling domains that act in a stimulatory manner may contain signaling motifs which are known as ITAMs. The secondary or co-stimulatory signaling domains that act in a stimulatory manner may contain signaling motifs which are known as CMs.

Examples of ITAM containing primary signaling domains that are of particular use in the present invention include those derived from TCR zeta, FcR gamma, FcR beta, CD3 gamma, CD3 delta, CD3 epsilon, CD5, CD22, CD79a, CD79b, and CD66d. Preferably, the signaling molecule (i.e. ITAM) of the CAR of the present invention comprises a signaling sequence derived from CD3 zeta.

In a preferred embodiment, the ITAM of the signaling domain of the CAR can be designed to comprise the CD3-zeta signaling domain by itself or combined with any other desired cytoplasmic domain(s) useful in the context of the CAR of the present invention. For example, the cytoplasmic domain of the CAR can comprise a CD3 zeta chain portion and a costimulatory signaling region. The costimulatory signaling region refers to a portion of the CAR comprising the intracellular domain of the CM. The CM is a cell molecule other than an antigen receptor that are required for an efficient response of lymphocytes to an antigen. Examples of such molecules include CD27, CD28, 4-1BB/CD137, OX40, CD30, CD40, PD-1, ICOS, HVEM, lymphocyte function-associated antigen-1 (LFA-1), CD2, CD7, LIGHT, NKG2C, B7-H3, and a ligand that specifically binds to CD83, and the like. Thus, while the present invention involves primarily with 4-1BB/CD137 as the co-stimulatory signaling molecule, other costimulatory molecules are within the scope of the invention.

The ITAM and the CM within the cytoplasmic signaling domain portion of the CAR of the invention may be linked to each other in a random or specified order. Optionally, a short oligo- or polypeptide linker, preferably about between 2 and 10 amino acids in length may form the linkage. A glycine-serine doublet provides a particularly suitable linker.

In some embodiments, the signaling domain is designed to comprise not only the ITAM but also the CM domain including CD27, CD28, CD30, 4-1BB/CD137, OX40, HVEM or any combination thereof. In another embodiment, the CM of the signaling domain in the intracellular portion of the CAR comprises 4-1BB/CD137. In a preferred embodiment, the signaling domain is designed to comprise the ITAM of CD3-zeta and the CM of 4-1BB/CD137.

Vectors

The present invention encompasses a DNA vector construction comprising a nucleic acid sequence of CAR. Further, the nucleic acid sequence includes the nucleic acid sequence of an antigen-binding fragment operably linked to the nucleic acid sequence of a transmembrane domain and a signaling domain. The nucleic acid sequences coding for the desired molecules can be obtained using recombinant methods known in the art, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors for inserting a DNA of the present invention. The vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-dividing cells, such as hepatocytes. They also have the added advantage of low immunogenicity.

Briefly, the expression of natural or synthetic nucleic acids encoding CARs is achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, under standard gene delivery protocols. In another embodiment, the invention provides a gene therapy vector.

The nucleic acid can be cloned into some types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be infected into a cell in the form of a viral vector. Viral vector technology is well known in the art. Viruses, which are useful as vectors include, but are not limited to, retroviruses, adenoviruses, adeno-associated viruses, herpes viruses, and lentiviruses. Generally, a suitable vector contains an origin of replication functional in at least one organism, a promoter sequence, convenient restriction endonuclease sites, and one or more selectable.

Some viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. Some retroviral systems are known in the art. In some embodiments, lentivirus vectors are used.

In order to assess the expression of CAR, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein (GFP) gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription. In some embodiments, the GFP is used.

Methods of introducing and expressing genes in a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, gene gun, and the like. Methods for producing cells comprising vectors and/or exogenous nucleic acids are well-known in the art. A preferred method for the introduction of a polynucleotide into a host cell is electroporation transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from a lentivirus, poxviruses, herpes simplex virus I, adenoviruses and adeno-associated viruses, and the like.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Regardless of the method used to introduce exogenous nucleic acids into a host cell, to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Pharmaceutical Composition

The invention further provides a pharmaceutical composition including a population of a cell (e.g., lymphocyte) expressed at least one of artificial CAR protein or contained at least one of DNA vector construction of the artificial CAR. Therefore, the CAR cell exhibits an antitumor property.

Sources of Cells

Before expansion and genetic modification of the $CD3^+$ lymphocytes of the invention, a source of $CD3^+$ Lymphocytes is obtained from a subject. $CD3^+$ Lymphocytes can be obtained from numbers of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of $CD3^+$ Lymphocytes available in the art, may be used. In certain embodiments of the present invention, $CD3^+$ Lymphocytes can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments of the invention, the cells are washed with phosphate buffered saline (PBS). After washing, the cells may be re-suspended in a variety of biocompatible buffers, such as, for example, $Ca^{2+}$-free, $Mg^{2+}$-free PBS, or other saline solution with or without buffer. Alternatively, the undesirable components of the apheresis sample may be removed and the cells directly re-suspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as $CD2^+$ and $CD3^+$, can be further isolated by positive or negative selection techniques. For example, In some embodiments, T cells are isolated by incubation with anti-CD14, anti-CD16, anti-CD19, anti-CD36, anti-CD56, anti-CD123 and anti-Glycophorin A conjugated beads, such as MACS® Pan T Cell Isolation Kit II, for a time period sufficient for negative selection of the desired T cells. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic or flow cytometry that uses a cocktail of monoclonal antibodies directed to cell surface markers present on the cells negatively selected.

The source of the cells to be expanded can be collected at any time point necessary, and desired cells, such as T cells, isolated and frozen for later use in T cell therapy for any number of diseases or conditions that would benefit from T cell therapy, such as those described herein. In some embodiments, a blood sample or an apheresis is taken from a healthy subject. In another embodiment, a blood sample or an apheresis is taken from a healthy subject who is at risk of developing a disease, but who have not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but before any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. In a further embodiment, the cells are isolated from a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

Activation and Expansion of T Cells

Whether before or after genetic modification of the T cells to express a desirable CAR, the T cells can be activated and expanded using methods as described.

The T cells of the invention are expanded by contact with a surface having attached to it an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ or $CD8^+$ T cells, an anti-CD3 antibody and an anti-CD28 antibody are used. Examples of an anti-CD3 antibody include HIT3a, UCHT1 and OKT3 (BD Pharmingen™ USA) can be used as can other methods commonly known in the art (Kemper et al., Nature 421.6921: 388-92. 2003; Li et al., J. Immunother. 35(2): 189-95, 2012). Examples of an anti-CD28 antibody include CD28.2, L293 and clone 15E8 (BD Pharmingen™, USA) can be used as can other methods commonly known in the art as previous mention.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of force, such as a magnetic force, resulting in increased ligation of cell surface markers, thereby inducing cell stimulation.

In some embodiments of the present invention, the mixture may be cultured for several hours (about 3 hours) to about 14 days or any hourly integer value in between. In another embodiment, the mixture may be cultured for 21 days. In some embodiments of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., RPMI Media 1640 or LGM-3™ Lymphocyte Growth Medium (Lonza) or AIM-V) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled in the art. Other additives for the growth of cells include, but are not limited to, surfactant, plasmanate, and reducing agents such as N-acetyl-cysteine and 2-mercaptoethanol. Media can include RPMI 1640, DMEM, MEM, α-MEM, and F-12, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2).

T cells exposed to varied stimulation times may exhibit different characteristics. For example, typical blood or apheresed peripheral blood mononuclear cell products have a helper T cell population (TH, CD4$^+$) that is greater than the cytotoxic or suppressor T cell population (Tc, CD8$^+$). Ex vivo expansion of T cells by stimulating CD3 and CD28 receptors produces a population of T cells that prior to about days 8-9 consists predominately of TH cells, while after about days 8-9, the population of T cells comprises an increasingly greater population of Tc cells. Accordingly, depending on the purpose of treatment, infusing a subject with a T cell population comprising predominately of TH cells may be advantageous. Similarly, if an antigen-specific subset of Tc cells has been isolated it may be beneficial to expand this subset to a greater degree.

Therapeutic Application

The present invention encompasses a cell (e.g., T cell) transduced with a lentiviral vector (LV). For example, the LV encodes a CAR that combines an antigen recognition domain of a single-chain variable fragment, a transmembrane domain of CD8α and a signaling domain of CD3 zeta, 4-1BB/CD137, CD28 or any combinations thereof. Therefore, in some instances, the transduced T cell can elicit a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal with a popution of a T cell expressed a CAR.

In some embodiments, the present invention includes a type of cellular therapy where T cells are genetically modified to express a CAR and the CAR T cell is infused to a recipient in need thereof. The infused cell can kill tumor cells in the recipient. Unlike antibody therapies, CAR T cells can replicate in vivo resulting in long-term persistence that can lead to sustained tumor control.

In some embodiments, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. The anti-tumor immunity response elicited by the CAR-modified T cells may be an active or a passive immune response. Also, the CAR mediated immune response may be part of an adoptive immunotherapy approach in which CAR-modified T cells induce an immune response specific to the antigen binding moiety in the CAR. For example, a CAR19 T cells elicits an immune response specific against cells expressing CD19.

While the data disclosed herein specifically disclose lentiviral vector comprising anti-CD19 scFv derived from a monoclonal antibody, human CD8α hinge and transmembrane domain, and human 4-1BB/CD137 and CD3 zeta signaling domains, the invention should be construed to include any number of variations for each of the components of the construct as described elsewhere herein. That is, the invention includes the use of any antigen binding moiety in the CAR to generate a CAR-mediated T-cell response specific to the antigen binding moiety. For example, the antigen binding moiety in the CAR of the invention can target a tumor antigen for treating cancer.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors.

In some embodiments, the antigen bind moiety portion of the CAR of the invention is designed to treat a particular cancer. For example, the CAR designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like. In another embodiment, the cancers and the disorders can be treated using a combination of CARs that target CD19, CD20, CD22, and ROR1.

The CAR modified T cells of the invention may also serve as a type of vaccine for ex vivo immunization and/or in vivo therapy in a mammal. Preferably, the mammal is a human.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the modified CAR cell can be autologous with respect to the recipient. Alternatively, the cells can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR modified T cells of the invention are used in the treatment of CLL. In certain embodiments, the cells of the invention are used in the treatment of patients at risk for developing CLL. Thus, the present invention provides methods for the treatment or prevention of CLL comprising administering to a subject in need thereof, a therapeutically effective amount of the CAR-modified T cells of the invention.

The CAR modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials. The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intramuscularly, by intravenous (i.v.) injection, or intraperitoneally (i.p.). In some embodiments, the T cell compositions of the present invention are administered to a patient by intradermal or subcutaneous injection. In another embodiment, the compositions of T cells may be injected directly into a tumor, lymph node, or site of infection.

In further embodiments, the T cells may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, rapamycin, mycophenolic acid, steroids, FR901228, cytokines, and irradiation. In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. In another certain embodiment, the used chemotherapy protocol can select from the following procedures: (A) Flu/Cy-A: administrating Fludarabine 30 mg/m$^2$ daily for 3 days and Cyclophosphamide 300 mg/m$^2$ daily for 3 days; (B) Flu/Cy-B: administrating Fludarabine 30 mg/m$^2$ daily for 4 days and Cyclophosphamide 500 mg/m$^2$ daily for 2 days; or (C) Flu/Cy-C: administrating Fludarabine 25 mg/m$^2$ daily for 3 days and Cyclophosphamide 60 mg/m$^2$ daily for 1 days.

The dosage of the above treatments to be administered to a patient will vary with the precise nature of the condition being treated and the recipient of the treatment. The scaling of dosages for human administration can be performed according to art-accepted practices.

Experimental Example

The invention is further described in detail by reference to the following experimental example. This example is provided for purposes of illustration only, and is not intended to be limiting unless otherwise specified. Thus, the invention should in no way be construed as being limited to the following example, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working example therefore, specifically points out the preferred embodiments of the present invention, and is not to be construed as limiting in any way the remainder of the disclosure.

The materials and methods employed in these experiments are now described.

Material and Method

Anti-CD19 CAR Lentiviral Vector Production

The clones of the mouse anti-human CD19 scFvs were generated by Uwell Biopharma. Codon optimization of the anti-CD19 scFv sequences was performed to improve gene expression in human cells. According to the gene sequence of NCBI GenBank, these plasmids, anti-CD19-scFv-CD8α-CD137-CD3ζ were designed. All the sequences of the plasmids were confirmed by DNA sequencing (Genomics, Taiwan).

Lentiviral Production and Determination of Viral Titer

The HEK 293T cells were transfected with the lentiviral transfer vector DNA, together with the packaging plasmids pCMVdeltaR8.91 and pMD.G (Academia Sinica, Taiwan) using X-tremeGENE 9 (Roche, Basel, Switzerland). The supernatant containing lentiviral particles was collected and concentrated using Lenti-X Concentrator (Clontech Laboratories, Mountain View, Calif.). The viruses were aliquoted and frozen at −80° C. until ready to use for virus tittering. All the lentiviruses used in the experiments were from concentrated frozen stocks. Titers of the lentivirus were determined by SUP-T1 cells based on 3-fold serial dilution of the concentrated lentivirus. Shortly, 50 ul 3-fold serial diluted concentrated lentivirus from 1:3 to a final dilution of 1:2,187 ul per well was transferred to SUP-T1 cells (20,000 cells/100 ul/well) seeded in a single well of a 96-well plate and incubated overnight. Two days post transduction, the SUP-T1 cells were stained with Biotin-SP-conjugated AffiniPure Goat anti-mouse IgG,F(ab')2 fragment specific (Jackson ImmunoResearch, West Grove, Pa.) followed by PE-conjugated streptavidin (Jackson ImmunoResearch, West Grove, Pa.). The percentage of CAR-positive cells was analyzed using flow cytometry (FACSCalibur cytometer, Becton Dickinson) and FlowJo software. Only dilutions generating 1 to 20% of CAR-positive cells should be considered for titer calculation. The percentage of CAR-positive cells is multiplied by the number of cells (20,000) seeded per well, then divided by the actual volume of added crude supernatant (in ml) to determine the titer of lentivirus in the supernatant (transducing units/ml). Multiplicity of infection (MOI) is defined as the ratio of transducing units of viral particles to the number of target T cells.

Cell Lines

The HEK 293T cells and human leukemia cell lines SUP-T1, Raji and RS4;11 cells were purchased from the American Type Culture Collection (ATCC; Rockville, Md.). The SUP-T1 cells were used for lentivirus titer analysis. The human leukemia cell line K562 was purchased from the Bioresource Collection and Research Center (BCRC; Hsinchu, Taiwan). The Raji, RS4;11, SUP-T1 and K562 cells were maintained in RPMI-1640 (Invitrogen, Carlsbad, Calif.) and the HEK 293T cells was maintained in DMEM (HyClone; GE Healthcare, South Logan, Utah); media were supplemented with 10% fetal bovine serum (FBS; Gibco, Carlsbad, Calif.) and 100 mg/mL penicillin/streptomycin (Gibco, Carlsbad, Calif.).

Preparation of Fluorescence Tumor Cells

For the visualization of injected tumor cells in immunodeficient mice, the Raji cells were transduced with a Lentivirus-EF1alpha-MCS-IRES-Luciferase plasmid (Addgene, Cambridge, Mass.) and the single Raji-Luc cell with the highest expression of luciferase was sorted with a FACSAria cell sorter (BD Biosciences, San Jose, Calif.).

Human T Cells Transduction

Peripheral blood samples were obtained from discarded anonymized by-products of platelet donations from healthy adult donors granted by the Institutional Review Board of Kaohsiung Veterans General Hospital (Protocol number: VGHKS13-CT6-11). Mononuclear cells collected from the samples by centrifugation on a Lymphoprep density step (Nycomed, Oslo, Norway) were washed twice using medium. Human T cells were purified by negative selection with a mixture of CD14, CD16, CD19, CD36, CD56, CD123, and CD235a antibodies and magnetic separation (Pan T Cell Isolation Kit II; Miltenyi Biotec). The percentage of CD3 and CD56 expression of T cells was determined with CD3-PerCP and CD56-FITC (BD Biosciences, San Jose, Calif.) staining using flow cytometry (FACSCalibur cytometer, Becton Dickinson). Purified T cells were maintained in RPMI-1640 medium containing 10% FBS and recombinant human IL-2 (rHuIL-2, 50 IU/ml; Proleukin, Novartis Pharma) with anti-CD3/CD28 beads (Thermo Fisher Scientific, Carlsbad, Calif.) until virus transduction. Within 24 hours, T cells were transduced with thawed lentiviruses using the same MOI to generate the CAR-T cells possessing the different scFv-derived binding domains. The culture medium was changed every 2 days and then the cells were transferred to G-Rex 24-well culture plate (Wolson Wolf Manufacturing, Saint Paul, Minn.) for a total 8-day expansion culture. Further, the cells were transferred to G-Rex 24-well culture plate after culturing four days (i.e., at the fifth day) and harvest at the eighth day. The T cells were stained with Biotin-SP-conjugated AffiniPure Goat anti-mouse IgG,F(ab')2 fragment specific (Jackson ImmunoResearch, West Grove, Pa.) followed by PE-conjugated streptavidin (Jackson ImmunoResearch, West Grove, Pa.) to determine the percentage of CAR-positive T cells.

In Vitro Functional Assays

To verify the specific antitumor capacity of anti-CD19 CAR-T cells against B-cell malignancy, CD19 positive RS4;11 and Raji cells were used as target cells, whereas CD19 negative K562 cells was regarded as control cells. The anti-CD19 CAR-T cells and target cells were co-cultured in 96-well plates with indicated E:T ratios. After 24 hours, cells were harvested, washed and stained with PE-conjugated mouse anti-human CD19 antibody (BD Biosciences, San Jose, Calif.). The percentage of CD19 positive cells representing the level of residual leukemia cells was analyzed by FACSCalibur flow cytometry.

The supernatants were harvested for the analysis of IFN-γ production of the CAR-T cells in response to leukemia cells using ELISA kits (R&D Systems, Inc, Minneapolis, Minn.). The absorbance at 450 nm in each well was measured using a microplate reader (Anthos 2010, Biochrom Ltd., Cambridge, UK). Cytotoxicity assay was further analyzed to determine the specific anti-leukemia ability of CAR-T cells. The target cells were suspended in RPMI-1640 containing 10% FBS, labeled with calcein AM (BD Biosciences, San Jose, Calif.), and plated onto 96-well flat-bottom plates (Costar, Corning, N.Y.). The CAR-T cells, suspended in RPMI-1640 containing 10% FBS, were then added at various E:T ratios and co-cultured with the target cells for 4 h. Following this, the cells were stained with propidium iodide (Sigma-Aldrich, St. Louis, Mo.), and the cytotoxicity was assessed by flow cytometry on a FACSCalibur (Becton Dickinson) instrument enumerating the number of viable target cells (calcein AM-positive, propidium-iodide negative, and light scattering properties of viable cells).

Multi-Parameter Flow Cytometry

Cells were evaluated by flow cytometry either fresh after Ficoll-Paque processing or frozen. Multi-parametric immunophenotyping was performed on $4 \times 10^6$ total cells/condition. Cells were stained at a density of $1 \times 10^6$ cells/100 μl PBS for 30 minutes on ice using antibody and reagent concentrations recommended by the manufacturer, washed, and acquired using a modified LSRII (BD Immunocytometry systems) equipped with Blue (488 nm) Violet (405 nm), Green (532), and Red (633 nm) lasers and appropriate filter sets for the detection and separation of the above antibody combinations. A minimum of 100,000 CD3+ cells were acquired for each stain. For functional assays, cells were washed, stained for surface markers, and acquired as above; a minimum of 50,000 CD3+ events were collected for each staining condition. Compensation values were established using single antibody stains and were calculated and applied automatically by the instrument. Data were analyzed using FlowJo software (Version 8.8.4, Treestar).

Xenogeneic Lymphoma Models

To assess the persistence and antitumor effect of different CAR (UW022, UW026 and FMC63) modified CD3$^+$ lymphocytes in vivo, we used a severe combined immunodeficient (SCID)-lymphoma human xenograft model. Advanced Severe Immuno Deficiency (ASID) mouse (NOD.Cg-Prkdcsc$^{scid}$Il2rg$^{tm1Wjl}$/YckNarl) experiments were performed in accordance with the Kaohsiung Veterans General Hospital Institutional Animal Care and Use Committee.

The first step of experiment is to evaluate Raji/Luc$^+$ cells engraftment. Therefore, ASID mice (8-10-week old; Laboratory Animal Center, Taiwan; 5×10$^5$ per mouse) were injected intraperitoneally (i.p.) with Raji/Luc$^+$ (5×10$^5$ cells per mouse) at Day 0. Tumor engraftment was measured using the in vivo imaging system as following described. In brief, mice were injected intraperitoneally (i.p.) with D-luciferin potassium salt (3 mg/mouse; Perkin Elmer; Waltham, Mass.), and analyzed using the IVIS Spectrum (Caliper Life Sciences, Hopkinton, Mass.). Photons emitted from luciferase-expression cells were quantified using the Living Image 3.0 software program. Mice were euthanized when bioluminescence reached 1×10$^{10}$ photons/second, or earlier if they showed physical signs warranting euthanasia.

To further determine the antitumor effect of different anti-CD19 CAR (UW022, UW026, and FMC63) modified CD3$^+$ lymphocytes, the lymphocytes thereof are expanded. After, T cells transduced with anti-CD19 CAR (UW022, UW026, and FMC63) and mock-transduced T cells were resuspended (RPMI-1640 plus 10% FBS) and expanded for 8 days, and then injected i.p. (1×10$^7$ cells per mouse) 7 days (at Day 7) after Raji-Luc injection. As a control, a group of mice received tissue culture medium instead of T cells.

Statistical Analysis

Student's t-test was used to determine the statistical significance of differences between samples, and P<0.05 was accepted as indicating a significant difference. For the bioluminescence experiments, intensity signals were summarized using mean±s.d. at baseline and multiple subsequent time points for each group of mice.

EXAMPLES

The following examples are offered by way of example and are not intended to limit the scope of the invention in any manner.

Example 1

Various Artificial CAR19 T Cells Demonstrate Similar Expansion Profile

Figure 2:
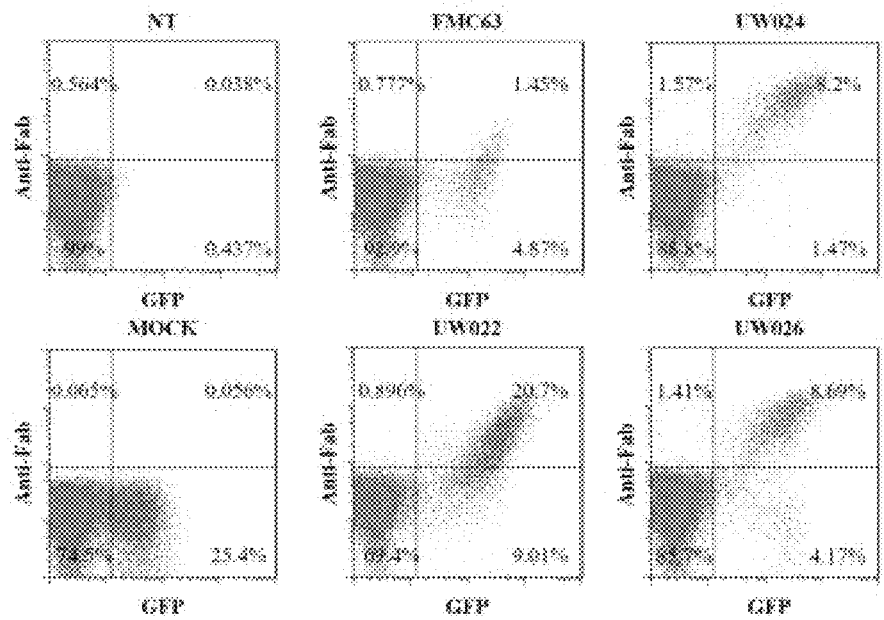
FIGS. 2A-2C are images of the schematic representations of the high expression efficiency and the high expansion rate of UW022-CAR, UW024-CAR or UW026-CAR modified $CD3^+$ lymphocytes.
Figure 2:
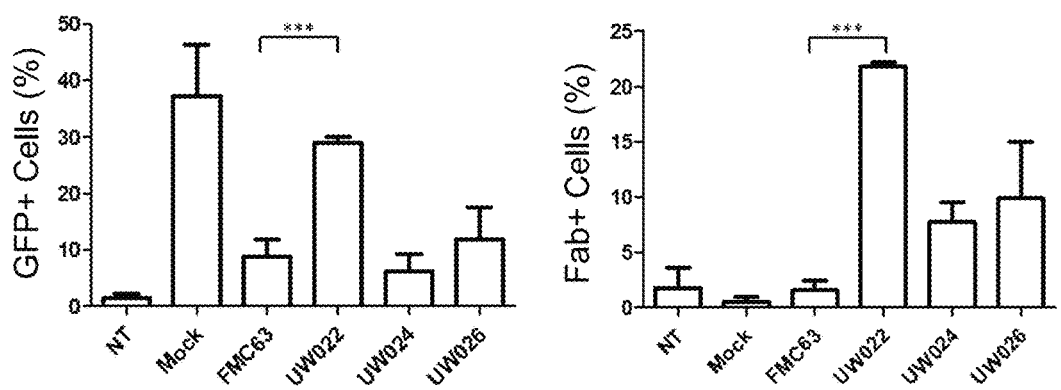
Figure 2:
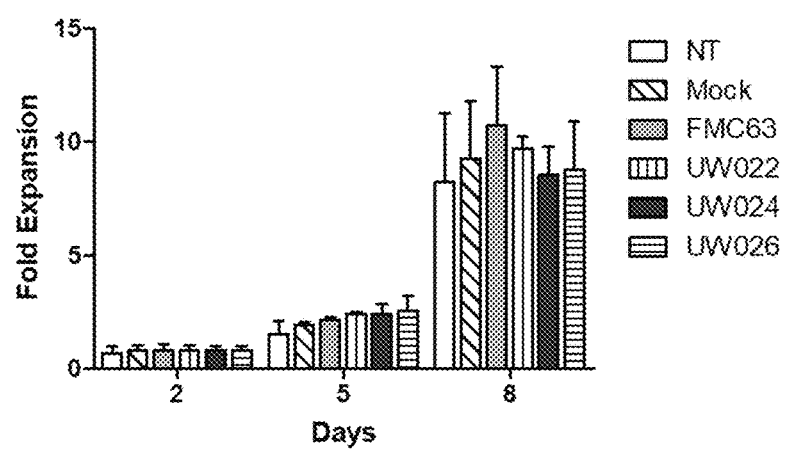

Three different artificial CAR19 expression vector, i.e. UW022, UW024 and UW026, are constructed as the previous description. Further, the artificial CAR19 generated by the UW022, UW024 and UW026 generally shares the similar composition that including a scFv in the CD19 antigen-binding fragment, a CD8α transmembrane domain and a signaling domain is consisted of a CD3 zeta chain (i.e., ITAM motif) and a 4-1BB/CD137 (i.e., CM motif.) Moreover, the amino acid combination of a heavy chain variable region and a light chain variable region of the scFv of the CAR19 in the UW022, UW024 and UW026 are SEQ ID NO: 8 with SEQ ID NO: 7, the SEQ ID NO: 10 with SEQ ID NO: 9, and the SEQ ID NO: 12 with SEQ ID NO: 11 respectively. The nucleic acid sequence combination of a heavy chain variable region and a light chain variable region of the scFv of the CAR19 in the UW022, UW024 and UW026 are SEQ ID NO: 2 with SEQ ID NO: 1, SEQ ID NO: 4 with SEQ ID NO: 3, and SEQ ID NO: 6 with SEQ ID NO: 5. In this experiment, another artificial CAR19 (i.e., FMC63) is used as the comparison. Through the GFP of the expression vector and the anti-Fab antibody, the transfection efficiency and the CAR19 protein expression of UW022, UW024 and UW026 can be detected. According to the quantitative results of GFP-positive CD3$^+$ lymphocytes (i.e., T cells) in FIGS. 2A and 2B, UW022-transfected T cells show the highest amount GFP-positive cells (29.71%) than others (UW024: 9.67%; UW026: 12.86%; or FMC63: 6.32%). That is the expression vector of UW022 shows the highest transfection efficiency compared to others modified CAR19 vectors. According to the quantitative results of Fab expression on primary human CD3$^+$ lymphocytes in FIGS. 2A and 2B, UW022 (21.6%), UW024 (9.77%) and UW026 (10.1%) all show that able to express the higher artificial CAR19 protein on CD3$^+$ lymphocytes surface than FMC63 (2.22%). Furthermore, it is worth to note that UW022 shows significantly higher efficiency to be transfected into the CD3$^+$ lymphocytes and then induces the CD3$^+$ lymphocytes to express higher amount of artificial CAR19 protein than FMC62 (as FIG. 2B shows). Taken together, the artificial CAR19 expression vector of UW022 shows both the high transfection efficiency and high expression efficiency compared to UW024, UW026 and FMC63. Although both UW024 and UW026 show the less ability of the transfection and the expression, both of them still demonstrate the higher alibies thereof compared to the FMC63. Additionally, UW024 and UW026 demonstrate the similar pattern (i.e., transfection efficiency and expression efficiency) with each other. To further determinate whether a bio-activity (i.e., proliferation ability/rate) of the modified T cells with UW022, UW024, UW026 or FMC63 (herein after "UW022-T cells, UW024-T cells, UW026-T cells or FMC63-T cells") is similar to or correlated with the above results. In other words, whether the UW022-T cells show the highest proliferation ability among the UW024-T cells, UW026-T cells or FMC63-T cells? The GFP and Fab double positive UW022-T cells, UW024-T cells, UW026-T cells or FMC63-T cells are purified and further cultured for the designed time. The proliferation ability of each group cells is examed by cell counting at day 2, 5 and 8 after culture. According to the FIG. 2C, cells growth rate of the UW022-T cells, UW024-T cells, UW026-T cells or FMC63-T cells are similar, therefore the proliferation ability thereof are similar.

Example 2

UW022-T Cells Demonstrate Highest Cytotoxicity Ability to CD19 Positive Tumor Cells To evaluate cytotoxicity ability of each modified CAR19 T cells (i.e., UW022-T cells, UW024-T cells, UW026-T cells or FMC63-T cells) to CD19 positive tumors, the certain modified CAR19 T cells are co-cultured with RS4;11 cells and Raji cells for indicating time and then analyzes a number of the CD19 positive cells through the flow cytometry after co-culture experiment. As the results of FIGS. 3A and 3B, although each of modified CAR19 T cells demonstrates that are capable of killing both CD19 positive tumor cells, the UW022-T cells show the highest cytotoxicity ability (only 4.01% of RS4;11 cells remain; only 0.41% of Raji cells remain) compared to others modified CAR19 T cells.

Figure 3:
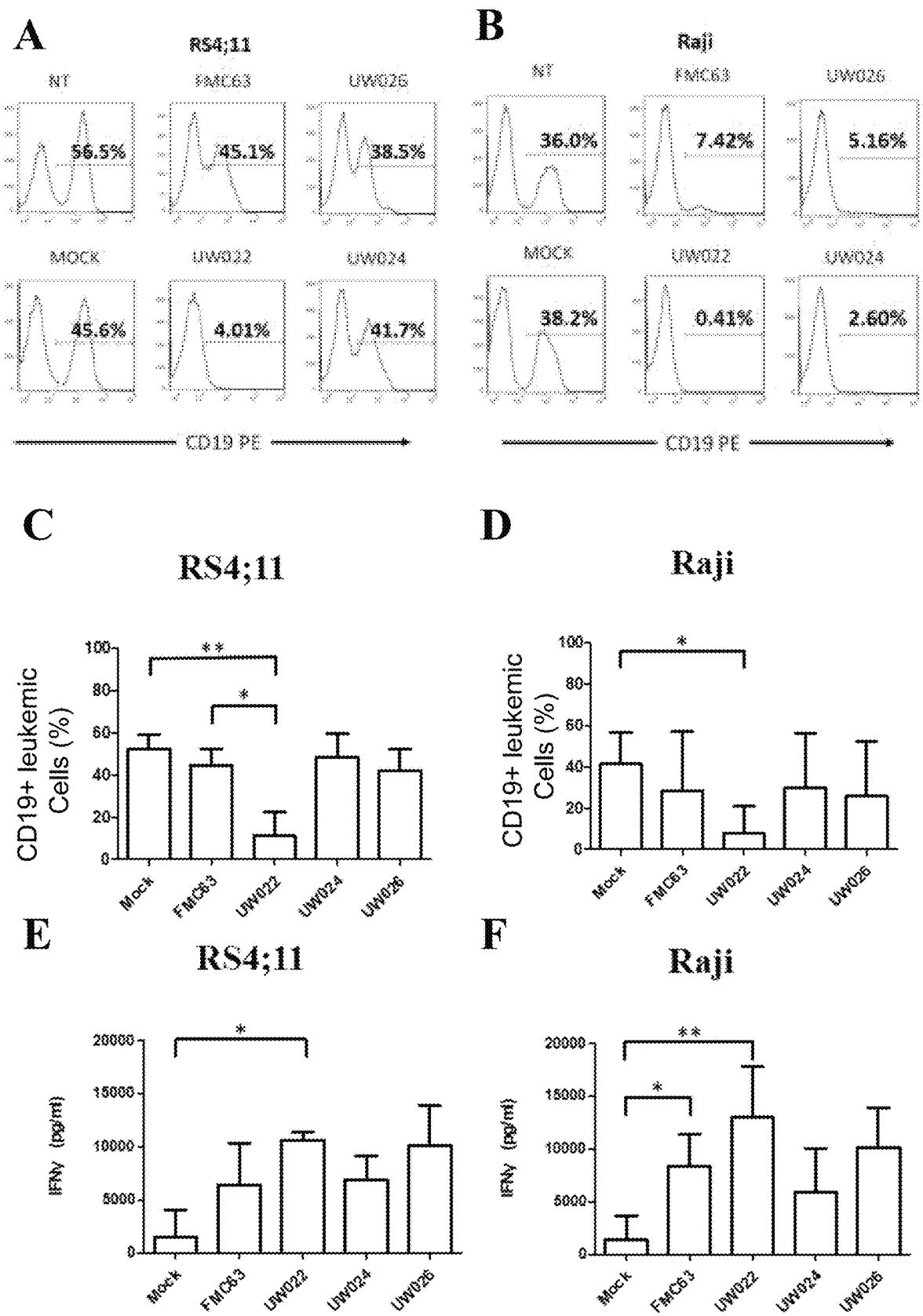
FIGS. 3A-3F are images of the schematic representations of the cytotoxicity efficiency of the CAR19 modified $CD3^+$ lymphocytes to two $CD19^+$ lymphoma cells (RS4;11 and Raji).

Regarding the results of the FIGS. 3A and 3C, although the UW024-T cells (41.70% of RS4;11 cells remain), UW026-T cells (38.50% of RS4;11 cells remain) and FMC63-T cells (45.10% of RS4;11 cells remain) show less cytotoxicity ability than UW022-T cells, both UW024-T cells and UW026-T cells still have higher ability than the FMC63-T cells to the RS4;11 tumor cells. Regarding the results of the FIGS. 3B and 3D, all of the CAR19 T cells show significant cytotoxicity ability to the Raji cells, however, the ability of the UW022-T cells (0.41% of Raji cells remain), the UW024-T cells (2.60% of Raji cells remain) and the UW026-T cells (5.16% of Raji cells remain) are still higher than the FMC63-T cells (7.42% of Raji cells remain).

For further confirming the results of cytotoxicity ability of FIG. 3A to 3D, the quantity of IFN-γ that secreted by the modified CAR19 T cells in the culture medium is analyzed through the enzyme-linked immunosorbent assay (the "ELISA assay"). According to the result of FIGS. 3E and 3F, the UW022-T cells is capable of secreting the highest amount of IFN-γ to the RS4;11 cells or the Raji cells compared with others modified CAR19 T cells. Furthermore, it is worth to note that UW022-T cells are capable of secreting significant higher amount of IFN-γ compared with the Mock treatment to the RS4;11 cells or the Raji cells. Therefore, the modified CAR19 T cells indeed have the cytotoxicity ability to the CD19 positive tumor cells (e.g., the RS4;11 cells and the Raji cells). Furthermore, the UW022-T cells demonstrate the significant cytotoxicity ability compared with others CAR19 T cells.

To further evaluate the limitation of cytotoxicity ability of each CAR19 T cells, we culture the certain CAR19 T cells with the tumor cells in the different ratio (e.g., the CAR19 T cells versus the tumor cells in 1:1, 2:1, 5:1 or 10:1). Furthermore, the tumor cells used herein include two CD19-positive tumors (i.e., RS4;11 and Raji) and one CD19-negative cell (i.e., K562). Regarding the results of K562 cells, all four modified CAR19 T cells show the similar cytotoxicity ability, and the ability correlates with the CAR19 T cell number. However, increasing the CAR19 T cells only slightly increases the ability (i.e., donor 1: form about 7% to about 17% and donor 2: from about 24% to about 40%).

Figure 4:
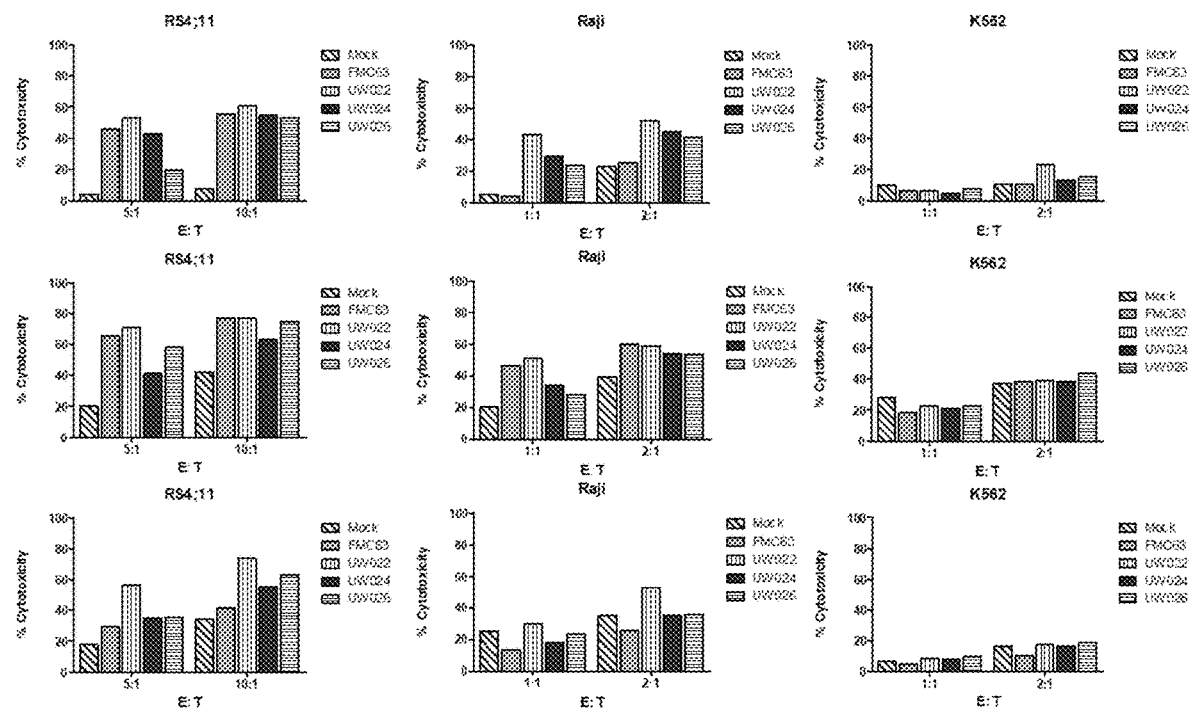
FIGS. 4A-4B are images of the schematic representations where the allogeneic cytotoxicity of the CAR19 modified $CD3^+$ lymphocytes to $CD19^+$ lymphoma cells (RS4;11 and Raji) is corresponding to the cell numbers of the modified $CD3^+$ lymphocytes.
Figure 4:
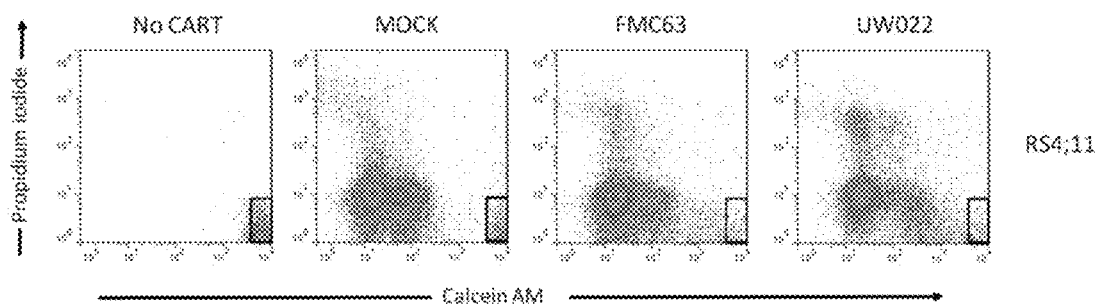

Regarding the results of RS4;11 and Raji cells, all four modified CAR19 T cells show the similar cytotoxicity ability that the ability correlates with the CAR19 T cell number. According to the results from Table 1 and FIG. 4A, the UW022-T cells show the highest cytotoxicity among all CAR19 T cells to RS4;11 or Raji cells. However, increasing the cell number of the UW022-T cells only slightly enhances the cytotoxic effect in both CD19-positive tumor groups. In another side, increasing others CAR19 T cells numbers may enhance the cytotoxicity to the tumor. For example, doubling the cells numbers of the UW026-T cells increases the cytotoxicity from 19.79% to 53.30% in the donor 1 group. Yet, only the UW022-T cells can result in the highest cytotoxicity in various ratio to the different tumor cells.

TABLE 1 the cytotoxicity of different ratio of CAR19 T cells to tumor cells

| Groups | RS4; 11 | | Raji | | K562 | |
| --- | --- | --- | --- | --- | --- | --- |
| | Ratio (CAR19 T cell: Tumor cell) | | | | | |
| | 5:1 | 10:1 | 1:1 | 2:1 | 1:1 | 2:1 |
| Donor 1 | | | | | | |
| Mock | 4.22% | 7.39% | 5.03% | 22.94% | 9.84% | 10.78% |
| FMC63 T cells | 45.78% | 55.80% | 4.17% | 25.29% | 6.33% | 10.30% |
| UW022-T cells | 52.90% | 60.95% | 43.43% | 51.99% | 6.20% | 22.85% |
| UW024-T cells | 42.74% | 54.88% | 29.39% | 44.99% | 4.52% | 12.73% |
| UW026-T cells | 19.79% | 53.30% | 23.91% | 41.30% | 7.51% | 15.49% |
| Donor 2 | | | | | | |
| Mock | 20.05% | 42.22% | 20.19% | 39.42% | 28.50% | 37.03% |
| FMC63 T cells | 65.64% | 77.08% | 46.37% | 59.85% | 18.54% | 38.25% |
| UW022-T cells | 70.66% | 76.88% | 50.67% | 58.66% | 22.49% | 39.33% |
| UW024-T cells | 41.44% | 63.10% | 33.98% | 53.29% | 20.93% | 38.60% |
| UW026-T cells | 57.93% | 74.78% | 27.92% | 53.68% | 22.96% | 43.55% |

We also used the flow cytometry assay to confirm the previous result. The previous treatment cells are further performed the double staining by propidium iodide (PI) and calcein-AM, and the staining cells are analysis through a flow cytometer. The PI and calcein-AM dyes were used to stain viable and dead cells, respectively. The calcein-AM dye only stains viable cells, and the PI only stains dead cells (i.e., necrosis cells). According to the result of FIG. 4B, the UW022-T cells induced a significant amount of PI positive but calcein-AM negative cells than the FMC63-T cells. That is, in conclusion, the UW022-T cells can effectively induce the tumor cells necrosis, which more specifically is the CD19 positive tumor cells.

Example 3

Figure 5:
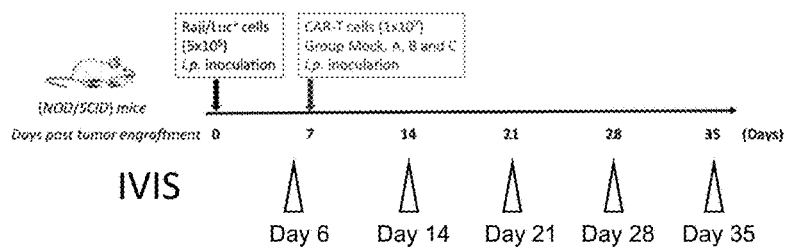
FIGS. 5A-5C is a series of images of the schematic representations of an in vivo cytotoxicity experiment design and in vivo cytotoxicity efficiencies of different modified $CD3^+$ lymphocytes.
Figure 5:
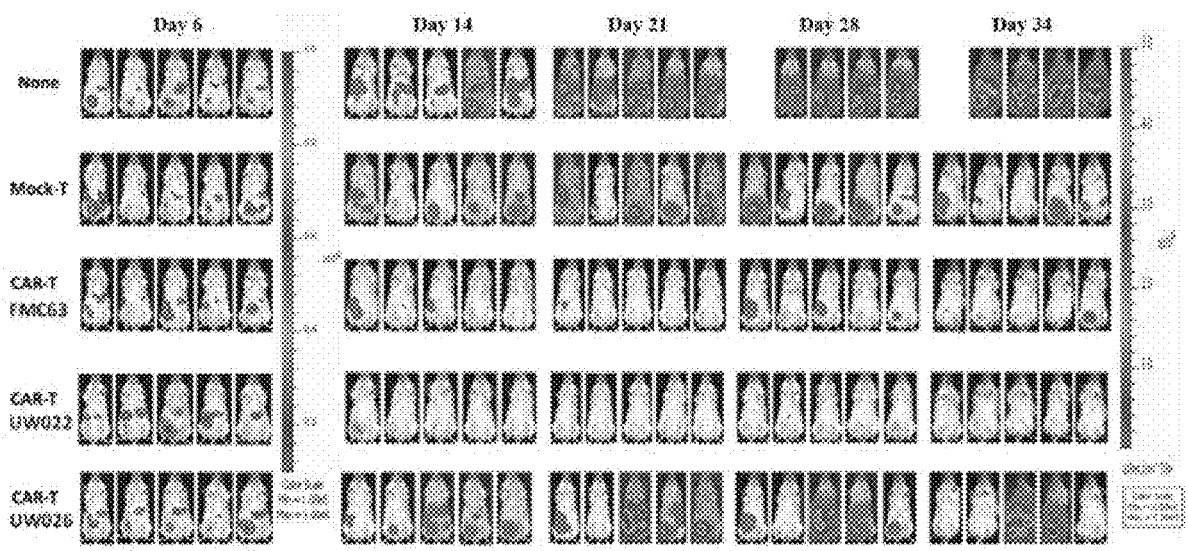
Figure 5:
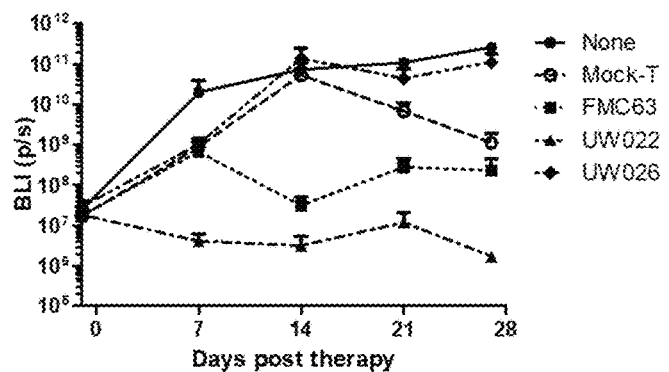

CAR19 T Cells Enhance the Cytotoxicity Ability to CD19 Positive Tumor Cells In Vivo To evaluate the persistence of our modified T cells in vivo, we used an ASID mouse lymphoma xenograft and an extensively validated bioluminescence imaging system (e.g., IVIS system). The ASID mouse lymphoma xenograft experiment design is as FIG. 5A shows. We began by evaluating the tumor engraftment after i.p. inoculation of Raji cells labeled with FFLuc at Day 0. After inoculating the FFLuc-labeled Raji cells, the growth of the FFLuc-labeled Raji cells in the ASID mouse were monitored by the IVIS system at Day 6, 14, 21, 28 and 34. We found that after infusion, Raji ($5\times10^5$ cells) had engrafted diffusely in lymph nodes and intraperitoneal (as the none-treatment group shows in FIG. 5B). After defining the timing and sites of tumor engraftment, we assessed T-cell trafficking to the tumor and T cell persistence in vivo. Control mock and three CAR19 T cells (FMC63-T, UW022-T and UW026-T) were infused ($1\times10^7$ cells/mouse) in mice after engrafting with labeled Raji cells. Specifically, the first step of the experiment is to induce the tumor model on the ASID mice through i.p. inoculation of Raji cells labeled with FFLuc into ASID mice at Day 0. After six days of i.p. inoculation (i.e., at Day 6), we use IVIS system to confirm that the inoculated FFLuc labeled Raji cells induce the solid tumor on the mice grew to the size that we expect. After confirming all the mice have the similar size of the solid tumor, we further treats the mice with control mock T cells and three CAR19 T cells (FMC63-T, UW022-T and UW026-T) at Day 7. We also use IVIS system to image the tumor growth every seven days (i.e., at Day 14, 21, 28 and 34) after treating mice with control mock T cells and three CAR19 T cells. Briefly, we only respectively inject the FFLuc labeled Raji cells and the various T cells into the mice once.

FIGS. 5B and 5C illustrate the development of Raji-engrafted tumor cells after infusing with various T cells. In one aspect, Raji bioluminescence is easily detectable when Raji was engrafted after 6 days (as the image in the Day 6 in the FIG. 5B shows). In another aspect, all T cells infused groups (e.g., the control mock T cell group and three CAR19 T cells group (e.g., FMC63-T, UW022-T and UW026-T)) show the less Raji bioluminescence signal than none treatment group. Yet, two of UW026-T cells treatment mice demonstrate the contrary results (i.e., abundant Raji cells development). As FIGS. 5B and 5C show, mock-T cells also capable of decreasing and delaying the tumor development compared with none treatment group. However, only FMC63-T and UW022-T cells significantly inhibit the solid tumor development. Importantly, UW022-T cells show the highest efficiency to inhibit the Raji cells development compared with FMC63-T cells. After engrafting UW022-T cells, the bioluminescence signal of the tumor cells in the mice of the UW022-T treatment group barely increases in the following detection compared with others treatment group or none treatment group. On other words, the tumor size on the mice of the UW022-T treatment group does not significantly increase compared with others groups. In conclusion, UW022-T cells also demonstrate the higher cytotoxicity than FMC63-T cells in vivo.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, manufacture, composition, methods and steps described in the specification. As one of ordinary skill in the art will readily appreciate from the disclosure of the present disclosure, processes, manufacture, compositions, methods, or steps, presently existing or later to be developed, that perform substantially the same function or achieve substantially the same result as the corresponding embodiments described herein may be utilized according to the present disclosure. Accordingly, the appended claims are intended to include within their scope such processes, manufacture, compositions, methods, or steps.

What is claimed is:

1. An expression vector of an artificial chimeric antigen receptor (CAR), comprising:
    a CD 19 antigen-binding fragment sequence comprising a nucleic acid sequence encoding a heavy chain variable domain, a light chain variable domain and a linker,
    wherein the nucleic acid sequence of the heavy chain variable domain is SEQ ID NO: 2 and the nucleic acid sequence of the light chain variable domain is SEQ ID NO: 1,
    or the nucleic acid sequence of the heavy chain variable domain is SEQ ID NO: 4 and the nucleic acid sequence of the light chain variable domain is SEQ ID NO: 3,
    or the nucleic acid sequence of the heavy chain variable domain is SEQ ID NO: 6 and the nucleic acid sequence of the light chain variable domain is SEQ ID NO: 5;
    a transmembrane domain sequence comprising a nucleic acid sequence encoding a transmembrane sequence of CD28, IgG1, CD4, CD8a or any combination thereof;
    and a signaling domain sequence comprising a nucleic acid sequence encoding at least one immunoreceptor tyrosine-based activation motif (ITAM) sequence, at least one co-stimulatory molecule (CM) sequence, or combination thereof.

2. The expression vector according to claim 1, wherein the transmembrane domain sequence is the transmembrane sequence of CD8a.

3. The expression vector according to claim 1, wherein a number of the at least one CM is at least two.

4. The expression vector according to claim 1, wherein the at least one ITAM comprises CD3 zeta.

5. The expression vector according to claim 1, wherein the sequence of the at least one CM comprises a CM sequence of CD27, CD28, CD30, 4-1BB/CD137, OX40, HVEM or any combination thereof.

6. The expression vector according to claim 5 wherein the at least one CM sequence comprises the CM sequence of 4-1BB/CD137.

7. A pharmaceutical composition comprising a population of modified cells, comprising: the artificial CAR a—according to claim 1, the expression vector of artificial CAR as according to claim 1.

8. The pharmaceutical composition according to claim 7, wherein the modified cell is a mammalian cell.

9. The pharmaceutical composition according to claim 7, wherein the modified cell is a mammalian lymphocyte.

10. The pharmaceutical composition according to claim 7, wherein the modified cell is a T cell or a NK cell.

* * * * *

SEQUENCE LISTING

```
<160> NUMBER OF SEQ ID NOS: 16

<210> SEQ ID NO 1
<211> LENGTH: 322
<212> TYPE: DNA
<213> ORGANISM: Artificial Sequence
<220> FEATURE:
<223> OTHER INFORMATION: Chemically Synthetic anti-CD19 Light Chain
      Variable Region - UW022L

<400> SEQUENCE: 1
gagatcgtgc tgacacagtc cccagccacc ctgtctctga gccctggaga gagggccacc      60
ctgtcctgct ctgccagctc cagcgtgagc tacatgcact ggtatcagca gaagccagga     120
caggcaccaa ggctgctgat ctacgacaca tctaagctgg ccagcggaat cccagcacgg     180
ttcagcggat ccggatctgg aaccgacttc accctgacca tcagctccct ggagccagag     240
gacgtggccg tgtactattg cttccagggc agcgtgtatc ccttcacatt tggccagggc     300
accaagctgg agatcaagag at                                              322

<210> SEQ ID NO 2
<211> LENGTH: 360
<212> TYPE: DNA
<213> ORGANISM: Artificial Sequence
<220> FEATURE:
<223> OTHER INFORMATION: Chemically Synthetic anti-CD19 Heavy Chain
      Variable Region - UW022H

<400> SEQUENCE: 2
caggtgcagc tgcaggagag cggaccagga ctggtgaagc cttcccagac actgtctctg       60
acatgtaccg tgtccggcgg cagcatctcc acctctggca tgggagtggg atggatcagg     120
cagcaccctg gcaagggcct ggagtggatc ggccacatct ggtgggacga tgacaagcgg     180
tacaacccag ccctgaagtc ccgggtgaca atcagcgtgg ataccctccaa gaatcagttc     240 tctctgaagc tgtcctctgt gacagccgcc gacaccgccg tgtactattg cgcccgcatg     300
gagctgtggt cctactattt tgattattgg ggccagggca cactggtgac cgtgagctcc     360
```

<210> SEQ ID NO 3
<211> LENGTH: 333
<212> TYPE: DNA
<213> ORGANISM: Artificial Sequence
<220> FEATURE:
<223> OTHER INFORMATION: Chemically Synthetic anti-CD19 Light Chain
      Variable Region - UW024L

<400> SEQUENCE: 3
gacatcctgc tgacccagac acctgcctcc ctggccgtgt ctctgggaca gagggcaacc        60
atcagctgca aggcctccca gtctgtggac tatgatggcg actcctatct gaactggtac       120
cagcagatcc caggccagcc ccctaagctg ctgatctacg atgccagcaa tctggtgtcc       180
ggaatcccac cacgcttcag cggatccgga tctggaaccg acttcaccct gaacatccac       240
cctgtggaga aggtggacgc cgccacctac cactgccagc agtccaccga ggatccatgg       300
acattcggcg gcggcaccaa gctggagatc aag                                    333

<210> SEQ ID NO 4
<211> LENGTH: 373
<212> TYPE: DNA
<213> ORGANISM: Artificial Sequence
<220> FEATURE:
<223> OTHER INFORMATION: Chemically Synthetic anti-CD19 Heavy Chain
      Variable Region - UW024H

<400> SEQUENCE: 4
caggtgcagc tgcagcagag cggagcagag ctggtgcgcc caggctctag cgtgaagatc        60
tcttgtaagg ccagcggcta tgccttttcc tcttactgga tgaattgggt gaagcagagg       120
ccaggacagg gactggagtg gatcggacag atctggccag cgatggcga cacaaactat        180 aatggcaagt tcaagggcaa ggccaccctg acagccgacg agagctcctc taccgcctat       240
atgcagctga gctccctggc ctctgaggat agcgccgtgt actttgcgc ccggagagag        300 accacaaccg tgggcagata ctattacgcc atggactact ggggccaggg cacctccgtg       360
acagtgtcta gca                                                          373

<210> SEQ ID NO 5
<211> LENGTH: 333
<212> TYPE: DNA
<213> ORGANISM: Artificial Sequence
<220> FEATURE:
<223> OTHER INFORMATION: Chemically Synthetic anti-CD19 Light Chain
      Variable Region - UW026L

<400> SEQUENCE: 5
gagatcgtgc tgacacagag ccctgacttt cagtccgtga ccccaaagga gaaggtgaca        60
atcacctgca gggcctccga gtctgtggac accttcggca tctcttttat gaactggttc       120
cagcagaagc cagatcagag ccccaagctg ctgatccacg cagcctccaa tcagggatct       180
ggagtgccta gccgctttag cggatccgga tctggcacag acttcacact gaccatcaac       240
tccctggagg ccgaggatgc cgccacctac tattgccagc agtctaagga ggtgccattc       300
acatttggcg gcggcaccaa ggtggagatc aag                                    333

<210> SEQ ID NO 6
<211> LENGTH: 363
<212> TYPE: DNA
<213> ORGANISM: Artificial Sequence
<220> FEATURE:
<223> OTHER INFORMATION: Chemically Synthetic anti-CD19 Heavy Chain Variable Region - UW026H

<400> SEQUENCE: 6

```
gaggtgcagc tggtggagag cggcggcggc ctggtgcagc cggcggctc cctgcggctg      60
tcttgtgccg ccagcggctt caccttttct agctcctgga tgaattgggt gagacaggca    120
ccaggcaagg gactggagtg ggtgggaagg atctaccctg cgacggcga tacaaactat     180
aatggcaagt ttaagggccg cttcaccatc agccgggacg attctaagaa cagcctgtac    240
ctgcagatga attccctgaa gacagaggac accgccgtgt actattgcgc ccgctctggc    300
tttatcacca cagtgctgga cttcgattat tggggccagg gcacactggt gaccgtgtct    360
agc                                                                  363
```

<210> SEQ ID NO 7
<211> LENGTH: 107
<212> TYPE: PRT
<213> ORGANISM: Artificial Sequence
<220> FEATURE:
<223> OTHER INFORMATION: Chemically Synthetic anti-CD19 Light Chain Variable Region - UW022L

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Val Ala Val Tyr Tyr Cys Phe Gln Gly Ser Val Tyr Pro Phe Thr
                85                  90                  95

Phe Gly Gln Gly Thr Lys Leu Glu Ile Lys Arg
            100                 105

<210> SEQ ID NO 8
<211> LENGTH: 120
<212> TYPE: PRT
<213> ORGANISM: Artificial Sequence
<220> FEATURE:
<223> OTHER INFORMATION: Chemically Synthetic anti-CD19 Heavy Chain Variable Region - UW022H

<400> SEQUENCE: 8

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 9
<211> LENGTH: 111
<212> TYPE: PRT
<213> ORGANISM: Artificial Sequence
<220> FEATURE:
<223> OTHER INFORMATION: Chemically Synthetic anti-CD19 Light Chain
      Variable Region - UW024L

<400> SEQUENCE: 9

Asp Ile Leu Leu Thr Gln Thr Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 10
<211> LENGTH: 124
<212> TYPE: PRT
<213> ORGANISM: Artificial Sequence
<220> FEATURE:
<223> OTHER INFORMATION: Chemically Synthetic anti-CD19 Heavy Chain
      Variable Region - UW024H

<400> SEQUENCE: 10

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Ser Val Thr Val Ser Ser
        115                 120

<210> SEQ ID NO 11
<211> LENGTH: 111
<212> TYPE: PRT
<213> ORGANISM: Artificial Sequence
<220> FEATURE:

<223> OTHER INFORMATION: Chemically Synthetic anti-CD19 Light Chain
       Variable Region - UW026L

<400> SEQUENCE: 11

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Met Asn Trp Phe Gln Gln Lys Pro Asp Gln Ser Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Lys
                85                  90                  95

Glu Val Pro Phe Thr Phe Gly Gly Gly Thr Lys Val Glu Ile Lys
            100                 105                 110
```

<210> SEQ ID NO 12
<211> LENGTH: 121
<212> TYPE: PRT
<213> ORGANISM: Artificial Sequence
<220> FEATURE:
<223> OTHER INFORMATION: Chemically Synthetic anti-CD19 Heavy Chain
       Variable Region - UW026H

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Asn Gly Lys Phe
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Ser Gly Phe Ile Thr Thr Val Leu Asp Phe Asp Tyr Trp Gly
            100                 105                 110

Gln Gly Thr Leu Val Thr Val Ser Ser
        115                 120
```

<210> SEQ ID NO 13
<211> LENGTH: 18
<212> TYPE: PRT
<213> ORGANISM: Artificial Sequence
<220> FEATURE:
<223> OTHER INFORMATION: Chemically Synthetic Linker 1

<400> SEQUENCE: 13

```
Lys Glu Ser Gly Ser Val Ser Ser Glu Gln Leu Ala Gln Phe Arg Ser
1               5                   10                  15

Leu Asp
```

<210> SEQ ID NO 14
<211> LENGTH: 14

```
<212> TYPE: PRT
<213> ORGANISM: Artificial Sequence
<220> FEATURE:
<223> OTHER INFORMATION: Chemically Synthetic Linker 2

<400> SEQUENCE: 14

Glu Gly Lys Ser Ser Gly Ser Gly Ser Glu Lys Ser Thr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Chemically Synthetic Linker 3

<400> SEQUENCE: 15

Gly Ser Ala Gly Ser Ala Ala Gly Ser Gly Glu Phe
1               5                   10

<210> SEQ ID NO 16
<211> LENGTH: 46
<212> TYPE: PRT
<213> ORGANISM: Artificial Sequence
<220> FEATURE:
<223> OTHER INFORMATION: Chemically Synthetic Linker 4

<400> SEQUENCE: 16

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45
```